United States Patent
Bechtel et al.

(10) Patent No.: US 12,070,311 B2
(45) Date of Patent: *Aug. 27, 2024

(54) TISSUE OXYGEN SATURATION WITH QUALITY METRIC REPORTING

(71) Applicant: ViOptix, Inc., Newark, CA (US)

(72) Inventors: Kate LeeAnn Bechtel, Pleasant Hill, CA (US); Alex Michael Margiott, Dunbarton, NH (US); Jennifer Elizabeth Keating, Campbell, CA (US); Kimberly Merritt Shultz, Mountain View, CA (US); Scott E. Coleridge, New York, NY (US); Joseph Heanue, Oakland, CA (US)

(73) Assignee: ViOptix, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/114,185

(22) Filed: Feb. 24, 2023

(65) Prior Publication Data

US 2023/0240568 A1 Aug. 3, 2023

Related U.S. Application Data

(63) Continuation of application No. 17/037,545, filed on Sep. 29, 2020, now Pat. No. 11,589,784, which is a
(Continued)

(51) Int. Cl.
*A61B 5/1455* (2006.01)
*A61B 5/00* (2006.01)

(52) U.S. Cl.
CPC ........ *A61B 5/14552* (2013.01); *A61B 5/4848* (2013.01); *A61B 5/7221* (2013.01);
(Continued)

(58) Field of Classification Search
CPC . A61B 5/0205; A61B 5/1455; A61B 5/14551; A61B 5/14552; A61B 5/742;
(Continued)

(56) References Cited

U.S. PATENT DOCUMENTS 6,385,821 B1   5/2002   Modgil et al.
7,236,813 B2   6/2007   Parker
(Continued)

FOREIGN PATENT DOCUMENTS

EP   0102816 A2   3/1984
EP   1889569 B1   6/2014
(Continued)

OTHER PUBLICATIONS

International Search Report, PCT Application PCT/US2017/029220, Aug. 3, 2017, 3 pages.

*Primary Examiner* — Chu Chuan Liu
(74) *Attorney, Agent, or Firm* — Aka Chan LLP

(57) ABSTRACT

An oximeter probe determines an oxygen saturation for the tissue and determines a quality value for the oxygen saturation and associated measurements of the tissue. The quality value is calculated from reflectance data received at the detectors of the oximeter probe. The oximeter probe then displays a value for the oxygen saturation with the error value to indicate a quality level for the oxygen saturation and associated values used to calculate oxygen saturation.

21 Claims, 29 Drawing Sheets

Related U.S. Application Data continuation of application No. 15/495,194, filed on Apr. 24, 2017, now Pat. No. 10,786,187.

(60) Provisional application No. 62/326,673, filed on Apr. 22, 2016, provisional application No. 62/326,630, filed on Apr. 22, 2016, provisional application No. 62/326,644, filed on Apr. 22, 2016.

(52) U.S. Cl.
CPC ............ *A61B 5/7275* (2013.01); *A61B 5/742* (2013.01); *A61B 5/743* (2013.01); *A61B 5/7475* (2013.01); *A61B 2560/0214* (2013.01); *A61B 2560/0425* (2013.01); *A61B 2560/0475* (2013.01); *A61B 2562/0238* (2013.01); *A61B 2562/0242* (2013.01); *A61B 2562/046* (2013.01)

(58) Field of Classification Search
CPC ..... A61B 5/7275; A61B 5/743; A61B 5/4848; A61B 5/7221; A61B 5/7475; A61B 2560/0425; A61B 2560/0475; A61B 2560/0214; A61B 2560/0238; A61B 2560/046

See application file for complete search history.

(56) References Cited

U.S. PATENT DOCUMENTS

| | | |
|---|---|---|
| 7,532,919 B2 | 5/2009 | Soyemi et al. |
| 8,233,955 B2 | 7/2012 | Al-Ali et al. |
| 8,938,279 B1 | 1/2015 | Heaton, II et al. |
| 2003/0009092 A1 | 1/2003 | Parker |
| 2004/0034294 A1 | 2/2004 | Kimball et al. |
| 2006/0053522 A1 | 3/2006 | Kimbell |
| 2006/0211925 A1 | 9/2006 | Lamego et al. |
| 2007/0244377 A1 | 10/2007 | Cozad et al. |
| 2008/0242959 A1 | 10/2008 | Xu et al. |
| 2008/0319290 A1 | 12/2008 | Mao et al. |
| 2009/0253968 A1 | 10/2009 | Cho et al. |
| 2010/0005630 A1 | 1/2010 | Gitman et al. |
| 2010/0292549 A1 | 11/2010 | Shuler |
| 2010/0298728 A1 | 11/2010 | Addison et al. |
| 2011/0205535 A1 | 8/2011 | Soller et al. |
| 2011/0224518 A1 | 9/2011 | Tindi et al. |
| 2011/0276276 A1 | 11/2011 | Kashyap et al. |
| 2012/0289801 A1 | 11/2012 | Yamaguchi |
| 2013/0023743 A1 | 1/2013 | Al-Ali et al. |
| 2013/0317331 A1 | 11/2013 | Bechtel et al. |
| 2014/0046152 A1 | 2/2014 | Bechtel et al. |
| 2014/0049770 A1* | 2/2014 | Li ...................... A61B 5/1455 356/40 |
| 2014/0180043 A1 | 6/2014 | Addison et al. |
| 2014/0288386 A1 | 9/2014 | Zand et al. |
| 2015/0230758 A1 | 8/2015 | Ochs |

FOREIGN PATENT DOCUMENTS

| | | |
|---|---|---|
| WO | 2009090665 A1 | 7/2009 |
| WO | 2010011763 | 1/2010 |
| WO | 2010042264 A1 | 4/2010 |
| WO | 2014026200 | 2/2014 |

\* cited by examiner

| R1 S1 D1 | R2 S1 D2 | R3 S1 D3 | R4 S1 D4 | R5 S1 D5 | R6 S1 D6 | R7 S1 D7 | R8 S1 D8 | R1 S2 D1 | R2 S2 D2 | R3 S2 D3 | R4 S2 D4 | R5 S2 D5 | R6 S2 D6 | R7 S2 D7 | R8 S2 D8 | VA | VS |
|---|---|---|---|---|---|---|---|---|---|---|---|---|---|---|---|---|---|
| 0000 | 0001 | 0010 | 0011 | 0100 | 0101 | 0110 | 0111 | 1000 | 1001 | 1010 | 1011 | 1100 | 1101 | 1110 | 1111 | 0000 | 0000 |
| 0001 | 0001 | 0010 | 0011 | 0100 | 0101 | 0111 | 0111 | 1000 | 1001 | 1010 | 1011 | 1100 | 1101 | 1110 | 1111 | 0000 | 0000 |
| ... | ... | ... | ... | ... | ... | ... | ... | ... | ... | ... | ... | ... | ... | ... | ... | ... | ... |
| 11111 | 11111 | 11111 | 11111 | 11111 | 11111 | 11111 | 11111 | 11111 | 11111 | 11111 | 11111 | 11111 | 11111 | 11111 | 11111 | 11111 | 11111 |

TISSUE OXYGEN SATURATION WITH QUALITY METRIC REPORTING

CROSS-REFERENCE TO RELATED APPLICATIONS

This application is a continuation of U.S. patent application Ser. No. 17/037,545, filed Sep. 29, 2020, issued as U.S. Pat. No. 11,589,784 on Feb. 28, 2023, which is a continuation of U.S. patent application Ser. No. 15/495,194, filed Apr. 24, 2017, issued as U.S. Pat. No. 10,786,187 on Sep. 29, 2020, which claims the benefit of the following U.S. patent applications 62/326,630, 62/326,644, and 62/326,673, filed Apr. 22, 2016. These applications are incorporated by reference along with all other references cited in these applications.

BACKGROUND OF THE INVENTION

The present invention relates generally to optical systems that monitor oxygen levels in tissue. More specifically, the present invention relates to optical probes, such as oximeters, that include sources and detectors on sensor heads of the optical probes and that use locally stored simulated reflectance curves for determining oxygen saturation of tissue.

Oximeters are medical devices used to measure oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or person training for a marathon); and veterinary purposes (e.g., animal monitoring).

Pulse oximeters and tissue oximeters are two types of oximeters that operate on different principles. A pulse oximeter requires a pulse in order to function. A pulse oximeter typically measures the absorbance of light due to pulsing arterial blood. In contrast, a tissue oximeter does not require a pulse in order to function, and can be used to make oxygen saturation measurements of a tissue flap that has been disconnected from a blood supply.

Human tissue, as an example, includes a variety of light-absorbing molecules. Such chromophores include oxygenated hemoglobin, deoxygenated hemoglobin, melanin, water, lipid, and cytochrome. Oxygenated hemoglobin, deoxygenated hemoglobin, and melanin are the most dominant chromophores in tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving measurement accuracy; reducing measurement time; lowering cost; reducing size, weight, or form factor; reducing power consumption; and for other reasons, and any combination of these measurements.

In particular, assessing a patient's oxygenation state, at both the regional and local level, is important as it is an indicator of the state of the patient's local tissue health. Thus, oximeters are often used in clinical settings, such as during surgery and recovery, where it may be suspected that the patient's tissue oxygenation state is unstable. For example, during surgery, oximeters should be able to quickly deliver accurate oxygen saturation measurements under a variety of nonideal conditions. While existing oximeters have been sufficient for postoperative tissue monitoring where absolute accuracy is not critical and trending data alone is sufficient, accuracy is, however, required during surgery in which spot-checking can be used to determine whether tissue might remain viable or needs to be removed.

Therefore, there is a need for improved tissue oximeter probes and methods of making measurements using these probes.

BRIEF SUMMARY OF THE INVENTION

An oximeter probe utilizes a relatively large number of simulated reflectance curves to quickly determine the optical properties of tissue under investigation. The optical properties of the tissue allow for the further determination of the oxygenated hemoglobin and deoxygenated hemoglobin concentrations of the tissue as well as the oxygen saturation of the tissue.

In an implementation, the oximeter probe can measure oxygen saturation without requiring a pulse or heart beat. An oximeter probe of the invention is applicable to many areas of medicine and surgery including plastic surgery. The oximeter probe can make oxygen saturation measurements of tissue where there is no pulse. Such tissue may have been separated from the body (e.g., a flap) to be transplanted to another place in, on, or in the body. Aspects of the invention may also be applicable to a pulse oximeter. In contrast to an oximeter probe, a pulse oximeter requires a pulse in order to function. A pulse oximeter typically measures the absorption of light due to the pulsing arterial blood.

In an implementation, a method includes providing a tissue oximeter device comprising a nonvolatile memory storing simulated reflectance curves, where the nonvolatile memory retains the simulated reflectance curves even after the device is powered off; emitting light from at least one source of the tissue oximeter device into a tissue to be measured; receiving at a plurality of detectors of the tissue oximeter device light reflected from the tissue in response to the emitted light; and generating, by the detectors, a plurality of detector responses from the reflected light.

The method includes fitting the detector responses to the simulated reflectance curves stored in the nonvolatile memory to determine a plurality of absorption coefficient values for the tissue for a plurality of oximeter measurements; calculating an oximetry value for the tissue from a first absorption coefficient value of the plurality of absorption coefficient values for a first oximeter measurement of the plurality of oximeter measurements; based on the first absorption coefficient value of the plurality of absorption coefficient values, calculating a first quality metric value for the oximetry value for the first oximeter measurement; and calculating a second quality metric value based on the first quality metric value and at least a second absorption coefficient value of the plurality of absorption coefficient values for at least a second oximeter measurement. The display displays the oximetry value and the second quality metric value for the oximetry value.

In an implementation, a system includes an oximeter device comprising a probe tip comprises source structures and detector structures on a distal end of the device and a display proximal to the probe tip, where the oximeter device calculates an oxygen saturation value and a quality metric value associated with the oxygen saturation value, and displays the oxygen saturation value on the display and the quality metric value associated with the displayed oxygen saturation value, and the oximeter device is specially configured to: transmit light from a light source of an oximeter probe into a first tissue at a first location to be measured; receive light at a detector of the oximeter probe that is reflected by the first tissue in response to the transmitted light; determine an oxygen saturation value for the first tissue; calculate a quality metric value associated with the determined oxygen saturation value for the first tissue; and display the oxygen saturation value and the quality metric value associated with the displayed oxygen saturation value on the display.

In an implementation, a method includes providing a tissue oximeter device comprising a nonvolatile memory storing simulated reflectance curves, where the nonvolatile memory retains the simulated reflectance curves even after the device is powered off; emitting light from at least one source of the tissue oximeter device into a tissue to be measured; receiving at a plurality of detectors of the tissue oximeter device light reflected from the tissue in response to the emitted light; and generating, by the detectors, a plurality of detector responses from the reflected light.

A processor of the tissue oximeter fits the detector responses to the simulated reflectance curves stored in the nonvolatile memory to determine an absorption coefficient value for the tissue and calculates an oximetry value for the tissue from the absorption coefficient value.

Based on the absorption coefficient value the processor calculates a quality metric value for the oximetry value, and displays on a display of the oximeter device, the oximetry value and the quality metric value for the oximetry value.

In an implementation, a method includes providing a tissue oximeter device comprising a nonvolatile memory storing simulated reflectance curves, where the nonvolatile memory retains the simulated reflectance curves even after the device is powered off; emitting light from a first source structure and a second source structure of the tissue oximeter device into tissue to be measured; receiving at a plurality of detector structures of the tissue oximeter device, light reflected from the tissue in response to the emitted light; and generating, by the detector structures, a plurality of detector responses from the reflected light.

A processor of the tissue oximeter fits the detector responses to the simulated reflectance curves stored in the nonvolatile memory to determine an absorption coefficient value for the tissue to determine one or more best fitting simulated reflectance curves. The processor calculates a first error value for the detector responses to the one or more best fitting simulated reflectance curves and calculates a tissue measurement value for the tissue base on the absorption coefficient value. The processor calculates a difference between the detector responses for two of the detector structures that are symmetrically located with respect to each other about a point on a line connecting the first and second source structures. If the difference between the detector responses differ by a threshold amount or more, the processor generates a second error value based on the difference between the detector responses.

The processor calculates a third error value by adjusting the first error value using the second error value and assigns a quality metric value for the oximetry value to the third error value. The processor displays on a display of the oximeter device, the tissue measurement value and the quality metric value for the oximetry value.

In an implementation, a system includes a tissue oximeter device that includes a handheld housing; a processor positioned in the handheld housing; a nonvolatile memory, positioned in the handheld housing and coupled to the processor, storing code and simulated reflectance curves, where the nonvolatile memory retains the simulated reflectance curves even after the device is powered off; a display, accessible from an exterior of the handheld housing, coupled to the processor; and a battery positioned in the handheld housing, coupled to and providing power to the processor, the nonvolatile memory, and the display.

The oximeter device includes a plurality of source structures and a plurality of detector structures. The code stored in the memory controls the processor to control a first source structure and a second source structure of the plurality of source structures to emit light into tissue to be measured and control the plurality of detector structures to detect light reflected from the tissue in response to the emitted light. The code controls the processor to control the detector structures to generate a plurality of detector responses from the reflected light and fit the detector responses to the simulated reflectance curves stored in the nonvolatile memory to determine an absorption coefficient value for the tissue to determine one or more best fitting simulated reflectance curves.

The code controls the processor to calculate a first error value for the detector responses to the one or more best fitting simulated reflectance curves; calculate a tissue measurement value for the tissue base on the absorption coefficient value; and calculate a difference between the detector responses for two of the detector structures that are symmetrically located with respect to each other about a point on a line connecting the first and second source structures. If the difference between the detector responses differ by a threshold amount or more, the code controls the processor to generate a second error value based on the difference between the detector responses; calculate a third error value by adjusting the first error value using the second error value; assign a quality metric value for the oximetry value to the third error value; and display on a display of the oximeter device, the tissue measurement value and the quality metric value for the oximetry value.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 9 shows a table for a database for a homogeneous model of tissue of simulated reflectance curves that is stored in the memory of the oximeter probe in an implementation.

FIGS. 11A-11B show a table for a database for a layered model of tissue where each row in the database is for four simulated reflectance curves for the four wavelengths of light emitted from the simulated source structures and detected by the simulated detector structures.

DETAILED DESCRIPTION OF THE INVENTION

Figure 1:
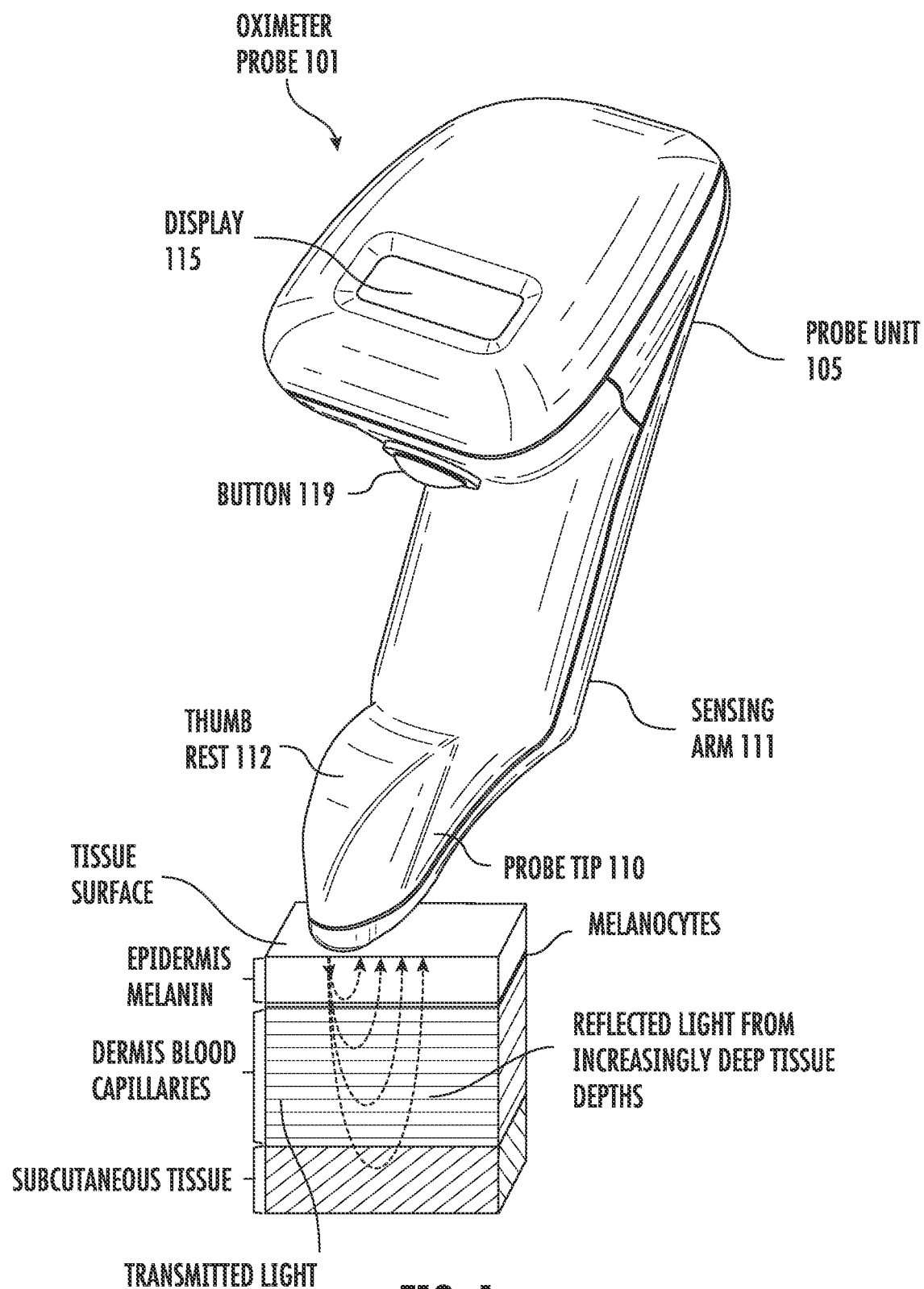
FIG. 1 shows an implementation of an oximeter probe.

FIG. 1 shows an image of an oximeter probe 101 in an implementation. Oximeter probe 101 is configured to make tissue oximetry measurements, such as intraoperatively and postoperatively. Oximeter probe 101 may be a handheld device that includes a probe unit 105, probe tip 110 (also referred to as a sensor head), which may be positioned at an end of a sensing arm 111. Oximeter probe 101 is configured to measure the oxygen saturation of tissue by emitting light, such as near-infrared light, from probe tip 110 into tissue, and collecting light reflected from the tissue at the probe tip.

Oximeter probe 101 includes a display 115 or other notification device that notifies a user of oxygen saturation measurements or other measurements made by the oximeter probe. While probe tip 110 is described as being configured for use with oximeter probe 101, which is a handheld device, probe tip 110 may be used with other oximeter probes, such as a modular oximeter probe where the probe tip is at the end of a cable device that couples to a base unit. The cable device might be a disposable device that is configured for use with one patient and the base unit might be a device that is configured for repeated use. Such modular oximeter probes are well understood by those of skill in the art and are not described further.

The following patent applications describe various oximeter devices and oximetry operation, and discussion in the following applications can be combined with aspects of the invention described in this application, in any combination. The following patent application are incorporated by reference along with all references cited in these application Ser. No. 14/944,139, filed Nov. 17, 2015, Ser. No. 13/887,130, filed May 3, 2013, Ser. No. 15/163,565, filed May 24, 2016, Ser. No. 13/887,220, filed May 3, 2013, Ser. No. 15/214,355, filed Jul. 19, 2016, Ser. No. 13/887,213, filed May 3, 2013, Ser. No. 14/977,578, filed Dec. 21, 2015, Ser. No. 13/887,178, filed Jun. 7, 2013, Ser. No. 15/220,354, filed Jul. 26, 2016, Ser. No. 13/965,156, filed Aug. 12, 2013, Ser. No. 15/359,570, filed Nov. 22, 2016, Ser. No. 13/887,152, filed May 3, 2013, Ser. No. 29/561,749, filed Apr. 16, 2016, 61/642,389, 61/642,393, 61/642,395, and 61/642,399, filed May 3, 2012, 61/682,146, filed Aug. 10, 2012, Ser. Nos. 15/493,132, 15/493,111, and 15/493,121, filed Apr. 20, 2017, Ser. No. 15/494,444 filed Apr. 21, 2017, Ser. Nos. 15/495,194, 15/495,205, and 15/495,212, filed Apr. 24, 2017.

Figure 2:
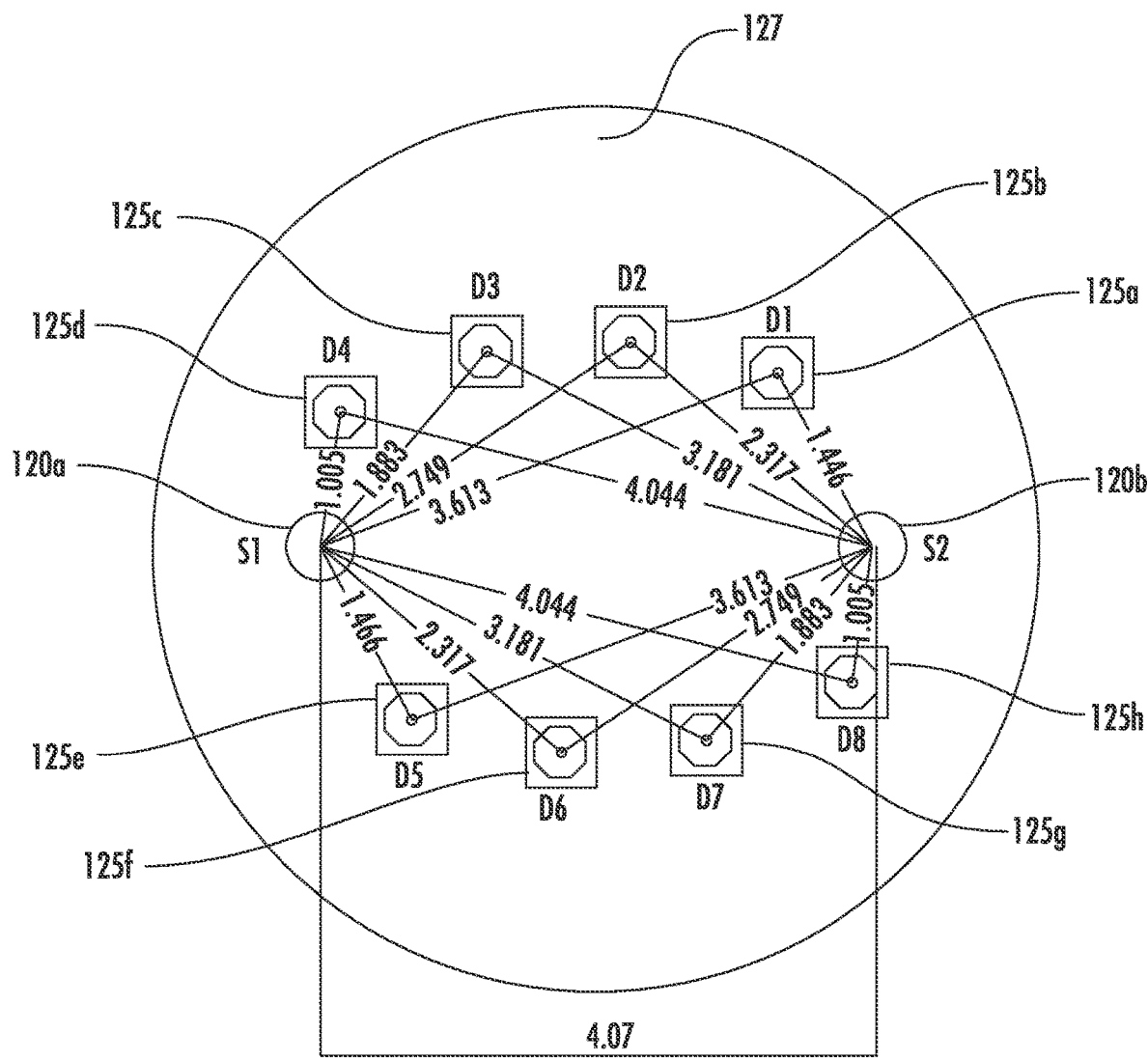
FIG. 2 shows an end view of the probe tip in an implementation.

FIG. 2 shows an end view of probe tip 110 in an implementation. Probe tip 110 is configured to contact tissue (e.g., a patient's skin) for which a tissue oximetry measurement is to be made. Probe tip 110 includes first and second source structures 120a and 120b (generally source structures 120) and includes first, second, third, fourth, fifth, sixth, seventh, and eighth detector structures 125a-125h (generally detector structures 125). In alternative implementations, the oximeter probe includes more or fewer source structures, includes more or fewer detector structures, or both.

Each source structure 120 is adapted to emit light (such as infrared light) and includes one or more light sources, such as four light sources that generate the emitted light. Each light source can emit one or more wavelengths of light. Each light source can include a light emitting diode (LED), a laser diode, an organic light emitting diode (OLED), a quantum dot LED (QMLED), or other types of light sources.

Each source structure can include one or more optical fibers that optically link the light sources to a face 127 of the probe tip. In an implementation, each source structure includes four LEDs and includes a single optical fiber that optically couples the four LEDs to the face of the probe tip. In alternative implementations, each source structure includes more than one optical fiber (e.g., four optical fibers) that optically couples the LEDs to the face of the probe tip.

Each detector structure includes one or more detectors. In an implementation, each detector structure includes a single detector adapted to detect light emitted from the source structures and reflected from tissue. The detectors can be photodetectors, photoresistors, or other types of detectors. The detector structures are positioned with respect to the source structures such that two or more (e.g., eight) unique source-to-detector distances are created.

In an implementation, the shortest source-to-detector distances are approximately equal. For example, the shortest source-to-detector distances are approximately equal between source structure 120a and detector structure 125d (S1-D4) and between source structure 120b and detector structure 125a (S2-D8) are approximately equal. The next longer source-to-detector distances (e.g., longer than each of S1-D4 and S2-D8) between source structure 120a and detector structure 125e (S1-D5) and between source structure 120b and detector structure 125a (S2-D1) are approximately equal. The next longer source-to-detector distances (e.g., longer than each of S1-D5 and S2-D1) between source structure 120a and detector structure 125c (S1-D3) and between source structure 120b and detector structure 125g (S2-D7) are approximately equal. The next longer source-to-detector distances (e.g., longer than each of S1-D3 and S2-D7) between source structure 120a and detector structure 125f (S1-D6) and between source structure 120b and detector structure 125b (S2-D2) are approximately equal. The next longer source-to-detector distances (e.g., longer than each of S1-D6 and S2-D2) between source structure 120a and detector structure 125c (S1-D2) and between source structure 120b and detector structure 125f (S2-D6) are approximately equal. The next longer source-to-detector distances (e.g., longer than each of S1-D2 and S2-D6) between source structure 120a and detector structure 125g (S1-D7) and between source structure 120b and detector structure 125c (S2-D3) are approximately equal. The next longer source-to-detector distances (e.g., longer than each of S1-D7 and S2-D3) between source structure 120a and detector structure 125a (S1-D1) and between source structure 120b and detector structure 125e (S2-D5) are approximately equal. The next longer source-to-detector distances (e.g., longest source-to-detector distance, longer than each of S1-D1 and S2-D5) between source structure 120a and detector structure 125h (S1-D8) and between source structure 120b and detector structure 125d (S2-D4) are approximately equal. In other implementations, the source-to-detector distance can all be unique or have fewer then eight distances that are approximately equal.

Table 1 below shows the eight unique source-to-detector distances according to an implementation. The increase between nearest source-to-detector distances is approximately 0.4 millimeters.

TABLE 1

| Source-to-Detector Pairs | Source-to-Detector Distances Millimeters |
|---|---|
| (S1-D4) | 1.005 |
| (S2-D8) | 1.005 |
| (S1-D5) | 1.446 |
| (S2-D1) | 1.446 |
| (S1-D3) | 1.883 |
| (S2-D7) | 1.883 |
| (S1-D6) | 2.317 |
| (S2-D2) | 2.317 |
| (S1-D2) | 2.749 |
| (S2-D6) | 2.749 |
| (S1-D7) | 3.181 |

TABLE 1-continued

| Source-to-Detector Pairs | Source-to-Detector Distances Millimeters |
|---|---|
| (S2-D3) | 3.181 |
| (S1-D1) | 3.613 |
| (S2-D5) | 3.613 |
| (S1-D8) | 4.004 |
| (S2-D4) | 4.004 |

In an implementation, for each wavelength of light (e.g., two, three, four, or more wavelengths of light in the visible spectrum, such as red, IR, or both visible and IR) that the oximeter probe is configured to emit, the oximeter probe includes at least two source-detector distances that are less than approximately 1.5 millimeters, less than approximately 1.6 millimeters, less than approximately 1.7 millimeters, less than approximately 1.8 millimeters, less than approximately 1.9 millimeters, or less than approximately 2.0 millimeters, and two source-detector distances that are greater than approximately 2.5 millimeters and less than approximately 4 millimeters, less than approximately 4.1 millimeters, less than approximately 4.2 millimeters, less than approximately 4.3 millimeters, less than approximately 4.4 millimeters, less than approximately 4.5 millimeters, less than approximately 4.6 millimeters, less than approximately 4.7 millimeters, less than approximately 4.8 millimeters, less than approximately 4.95 millimeters, or less than approximately 5 millimeters.

In an implementation, detector structures 125a and 125e are symmetrically positioned about a point that is on a straight line connecting sources 120a and 120b. Detector structures 125b and 125f are symmetrically positioned about the point. Detector structures 125c and 125g are symmetrically positioned about the point. Detector structures 125d and 125h are symmetrically positioned about the point. The point can be centered between source structures 120a and 120b on the connecting line.

A plot of source-to-detector distance verses reflectance detected by detector structures 125 can provide a reflectance curve where the data points are well spaced along the x-axis. These spacings of the distances between source structures 120a and 120b, and detector structures 125 adds data redundancy and can lead to the generation of relatively accurate reflectance curves.

In an implementation, the source structures and detector structures can be arranged at various positions on the probe surface to give the distances desired (such as indicated above). For example, the two sources form a line, and there will be equal number of detectors above and below this line. And the position of a detector (above the line) will have point symmetry with another detector (below the line) about a selected point on the line of the two sources. As an example, the selected point may be the middle between the two sources, but not necessarily. In other implementations, the positioning can be arranged based on a shape, such as a circle, an ellipse, an ovoid, randomly, triangular, rectangular, square, or other shape.

Figure 3:
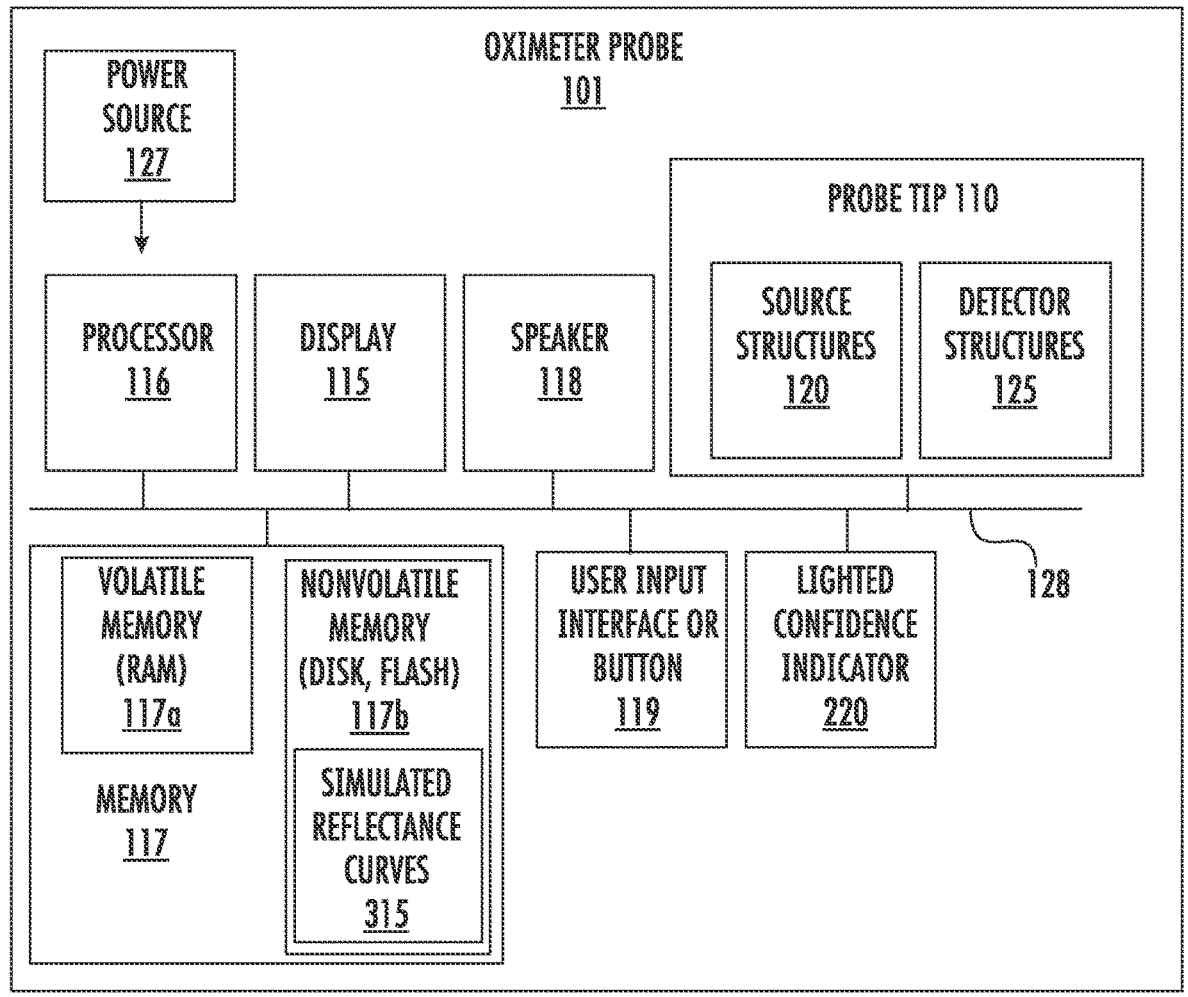
FIG. 3 shows a block diagram of an oximeter probe in an implementation.

FIG. 3 shows a block diagram of oximeter probe 101 in an implementation. Oximeter probe 101 includes display 115, a lighted quality indicator 220, a processor 116, a memory 117, a speaker 118, one or more user-selection devices 119 (e.g., one or more buttons, switches, touch input device associated with display 115), a set of source structures 120, a set of detector structures 125, and a power source (e.g., a battery) 127. The foregoing listed components may be linked together via a bus 128, which may be the system bus architecture of oximeter probe 101. Although this figure shows one bus that connects to each component, the busing is illustrative of any interconnection scheme serving to link these components or other components included in oximeter probe 101. For example, speaker 118 could be connected to a subsystem through a port or have an internal direct connection to processor 116. Further, the components described are housed in a mobile housing (see FIG. 1) of oximeter probe 101 in an implementation.

Processor 116 may include a microprocessor, a microcontroller, a multicore processor, or other processor type. Memory 117 may include a variety of memories, such as a volatile memory 117a (e.g., a RAM), a nonvolatile memory 117b (e.g., a disk or FLASH). Different implementations of oximeter probe 101 may include any number of the listed components, in any combination or configuration, and may also include other components not shown.

Power source 127 can be a battery, such as a disposable battery. Disposable batteries are discarded after their stored charge is expended. Some disposable battery chemistry technologies include alkaline, zinc carbon, or silver oxide. The battery has sufficient stored charged to allow use of the handheld device for several hours.

In other implementations, the battery is rechargeable where the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via an AC adapter with cord that connects to the handheld unit. The circuitry in the handheld unit can include a recharger circuit (not shown). Batteries with rechargeable battery chemistry may be sometimes used as disposable batteries, where the batteries are not recharged but disposed of after use.

Figure 4A:
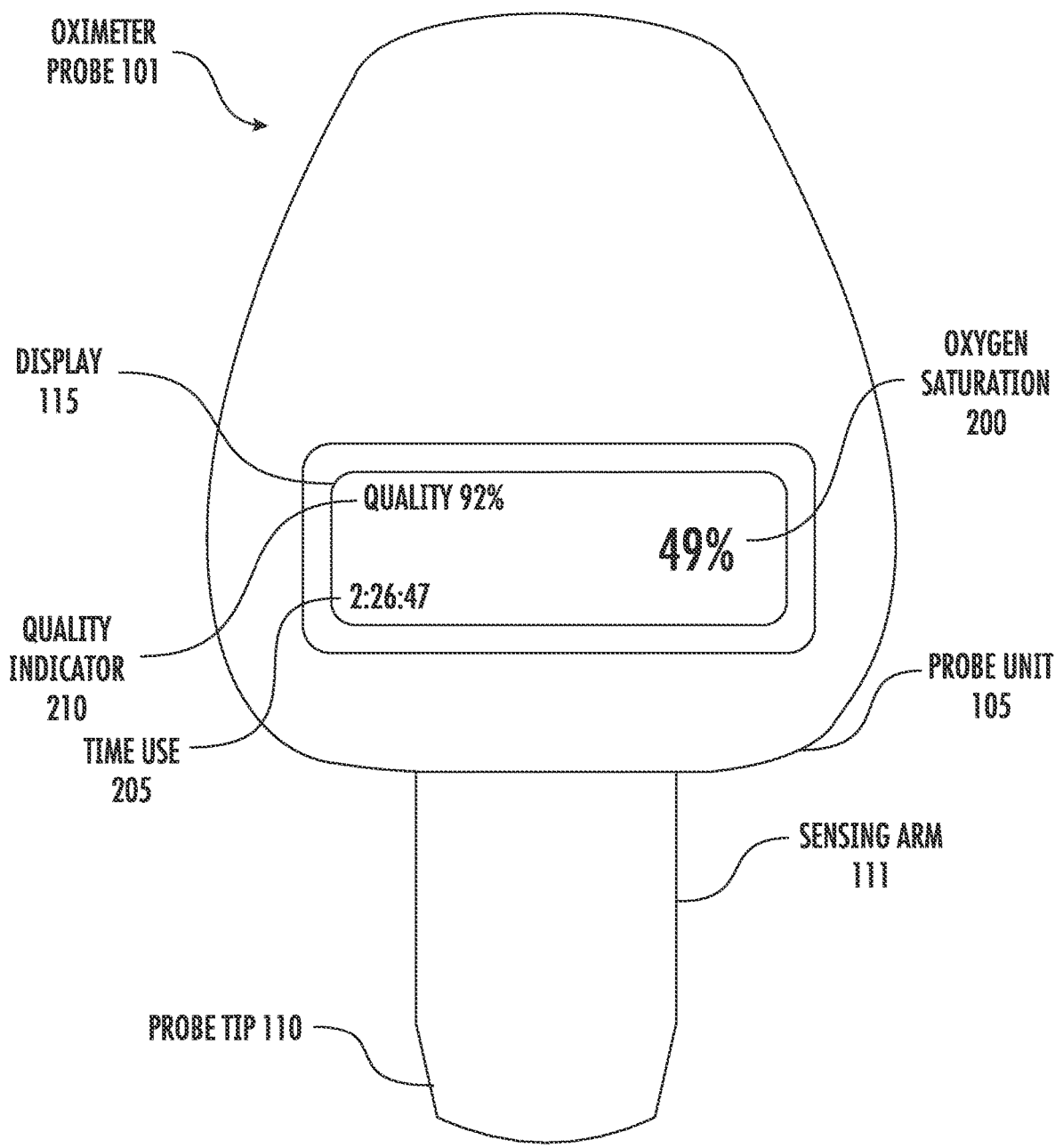
FIG. 4A shows a top view of the oximeter probe where the display of the probe displays a quality value as a percentage value for a measured valued of tissue that is measured by the probe.

FIG. 4A shows a top view of the oximeter probe 101 in an implementation. The top view shows the display 115 located in the probe unit 105 at a top portion of the oximeter probe. The display is adapted to display one or more pieces of information regarding the oximeter probe and measurement information for measurements made by the probe.

In an implementation, the display is adapted to display a value for the oxygen saturation 200 ("oxygen saturation value") of tissue that is measured by the oximeter probe. The display can display the oxygen saturation value as a percentage value (e.g., a ratiometric value), a bar graph with a number of bars (e.g., percentage value displayed as bars on the bar graph), via one or more colors (e.g., if the display is a color display), or with other displayable information. The display can also be adapted to display a value 205 for the duration for which the oximeter probe has been operating, for example, since a reset. The reset of the oximeter probe can occur when the batteries in the probe are changed, from a first power up on a previously unused set of batteries (fresh batteries), since a power up from a hard power down, since a power up from a soft power down (e.g., a hibernation mode), or other reset event.

The display is also adapted to display a quality value for the quality of the currently displayed measurement value. The quality value here is defined as a value associated with the confidence in the accuracy of the measurement as it was obtained. For example, if the probe is not in contact with the tissue, the quality metric would be a low value indicative of uncertainty in the accuracy of the measurement. The quality value may also be referred to as a quality metric, a quality indicator, a quality index, a confidence indicator, a confidence value, a confidence metric, or a confidence index.

The quality value can be for the oxygen saturation value that is displayed on the display. A quality value can also be reported for other information displayed on the display, such as a value for melanin content a value for blood volume, a value for oxygenated hemoglobin, a value for deoxygenated hemoglobin, or other values. The display can also be adapted to display two or more quality values. Each measurement value generated by the oximeter probe may be associated with one or more quality values. For example, if multiple quality values exist for a single measurement value (e.g. oxygen saturation value), these quality values may provide information regarding the confidence in proper detection of contributing factors to the calculation of a single measurement, such as the absorption coefficients, scattering coefficients, melanin content, or other chromophores. The quality value can be displayed as a percentage value (e.g., a ratiometric value), where the value represents the anticipated quality of a particular aspect of the measurement resulting in the oxygen saturation value.

The quality value can be based on one or more error values associated with the oxygen saturation value. For example, the quality value can be an error value for a fit of reflectance data to simulated reflectance curves 315 for tissue where the simulated reflectance curves are stored in memory 117. The reflectance data can be generated by the detector structures from detected light emitted from one or more of the source structures and reflected from tissue to the detector structures. The simulated reflectance curves can be generated from simulations of tissue for simulated light emitted into the tissue from simulated source structures and detected by simulated detector structures subsequent to reflection from or transmission through the simulated tissue. The simulated reflectance curves, fit to the curves, and the error value are described further below.

The quality indicator may also be based on a tiered scale, for instance descriptive words such as "acceptable," "unacceptable," "unclear." In this instance, bars in the bar graph may be used to indicate particular qualitative descriptions for the current measurement. The quality indicator may be used to provide feedback to the instrument operator. Such feedback may include methods to improve device contact with tissue. In an implementation, a user's manual for the oximeter probe or instruction presented on the display may provide the user feedback to improve the device contact with the tissue.

The quality value can be also be determined by the processor via comparison and assessment of the relationship between the reflectance at the detector structures and the reflectance data generated by the detector structures. This relationship can be based on raw data generated by the detector structures, filtered data, calibrated data, analog-to-digital converter (ADC) counts, or any other manipulation of the data. The quality value may be calculated by the processor based on relationships between two or more detectors and one or more sources. The quality value may be calculated based on detector data from one source location (e.g., source structure 120a) versus another source location (e.g., source structure 120b). The quality value determined by the processor can be based on ratiometric calculations or ascertained by comparing data distributions (e.g., through methods similar to the Bhattacharyya or Mahalanobis distance). The quality value may also be calculated by the processor based on the current relationship information among detectors compared with typical relationship information among the detectors that is stored in memory 117.

The quality value can be calculated by the processor using time domain feature analysis (e.g. variability over time, slope sign changes, and more) on the detector reference data. The quality value may be calculated by the processor via an evaluation of the relationship of time domain features among one, two, or more source-detector pairs.

Figure 4B:
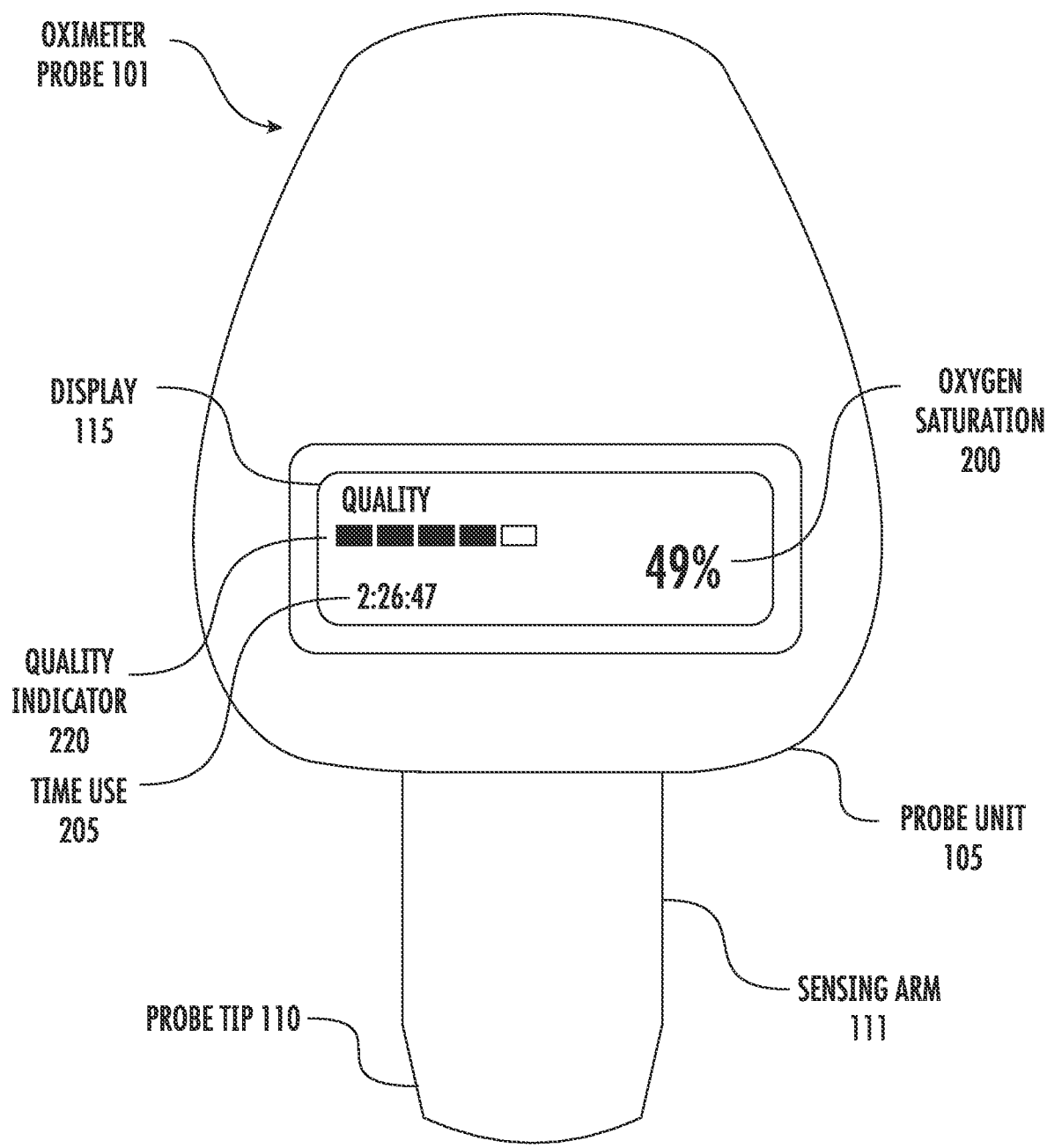
FIGS. 4B-4C show top views of the oximeter probe where the display of the probe displays a quality value via a bar graph for a measured valued of tissue that is measured by the probe.

FIG. 4B shows a top view of the oximeter probe 101 in an implementation. The display is adapted to display a bar graph 220 that represents a quality value (e.g., percentage value of the quality valued displayed as bars on the bar graph) for a displayed value that is displayed on the display. For example, the bar graph can represent a quality value for the oxygen saturation value 200 displayed on the display. The display can also be adapted to display two or more bar graphs for two or more quality values if the display displays two or more measurement values. Each bar graph is associated with one of the displayed measurement values.

Figure 4C:
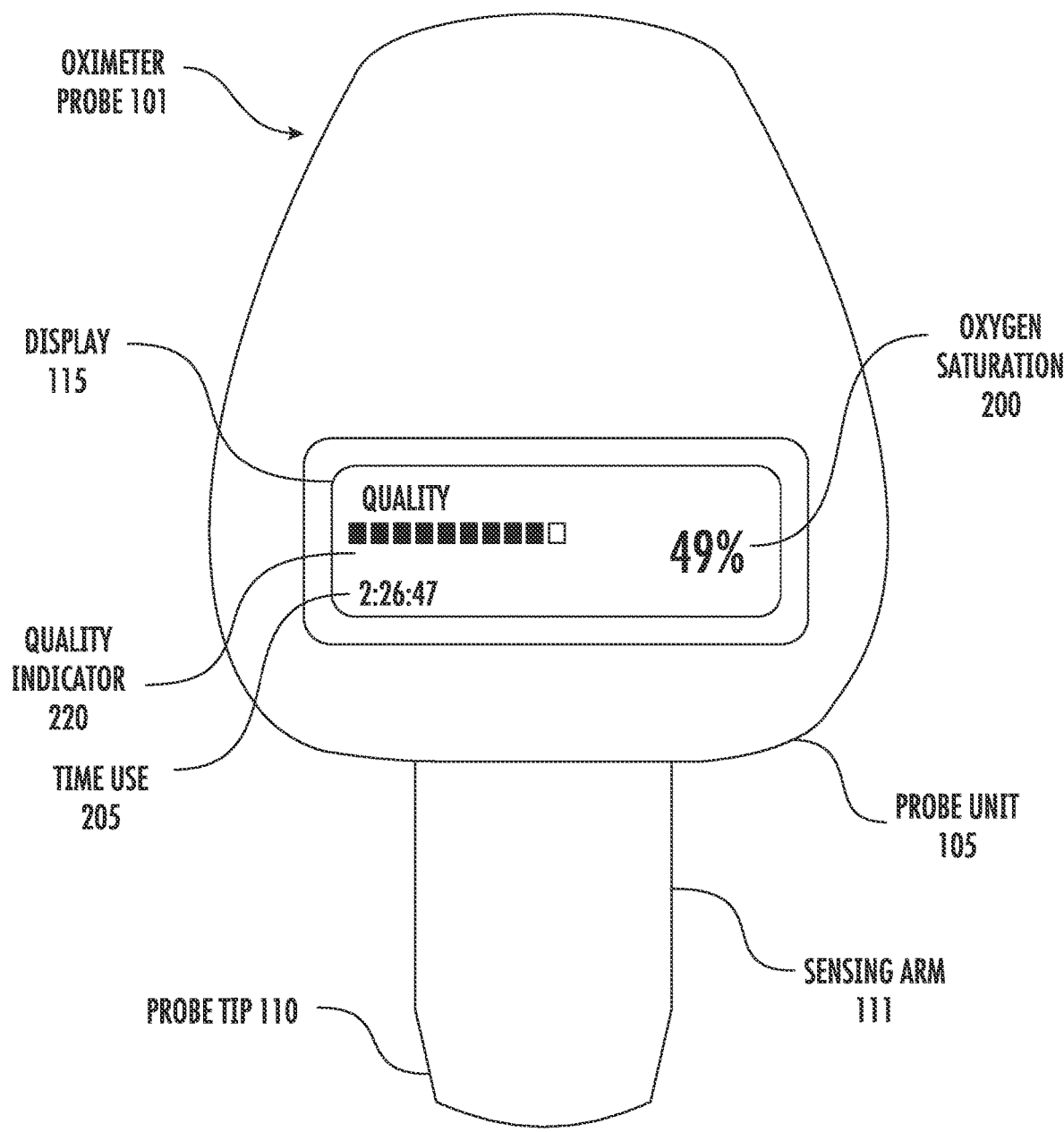

The bar graph can include two or more bars to indicate the quality value. For example, the bar graph can include 2 bars, 3 bars, 4 bars, 5 bars, 6 bars, 7 bars, 8 bars, 9 bars, 10 bars (FIG. 4C), or more bars. Each bar in the bar graph represents a range of quality values. The ranges represented by each of the bars can be the same or different. For example, the quality level required to fill the first bar (e.g. left most bar) may be higher than that required to fill the additional bars to the right. This may be achieved on a graded scale (e.g. decreasing percentage quality to fill bars) or on a scale that remains equal following the initial threshold quality value. For example, a graded scheme could consist of an initial quality value of 70 percent filling the first bar, followed by 85 percent for the second bar (15 percent step), 92.5 percent for the third bar (7.5-percent step), where the bars asymptotically approach 100 percent quality. An example of a scale that remains equal is a bar graph that includes six bars, and the first bar is configured to be activated at a 75 percent activation threshold, then the remaining five bars each represent a range of 5 percent for the quality value from 75 percent to approximately 100 percent.

The bars can be activated by a variety of techniques to indicate the activation or deactivation. For example, to indicate activation a bar can be lighted, darkened, lightened, filled with a fill color inside a surrounding border (e.g., as shown in FIG. 4B), fill color removed inside the surrounding border, or otherwise changed to indicate activation.

The quality value displayed via the bar graph can be based on one or more values associated with the oxygen saturation value or other displayed values. One type of value the quality value may be based on is an error value. Error values generated by the oximeter probe are described below. Quality can indicate the value of an aspect of a measurement, a calculation, a result of a calculation, or an intermediate result of a calculation leading to an oxygen saturation value where the oxygen saturation values is displayed with the quality value, but where the aspect for the measurement, the calculation, the result of a calculation, or the intermediate result of the calculation leading to the oxygen saturation value is not displayed.

Figure 4D:
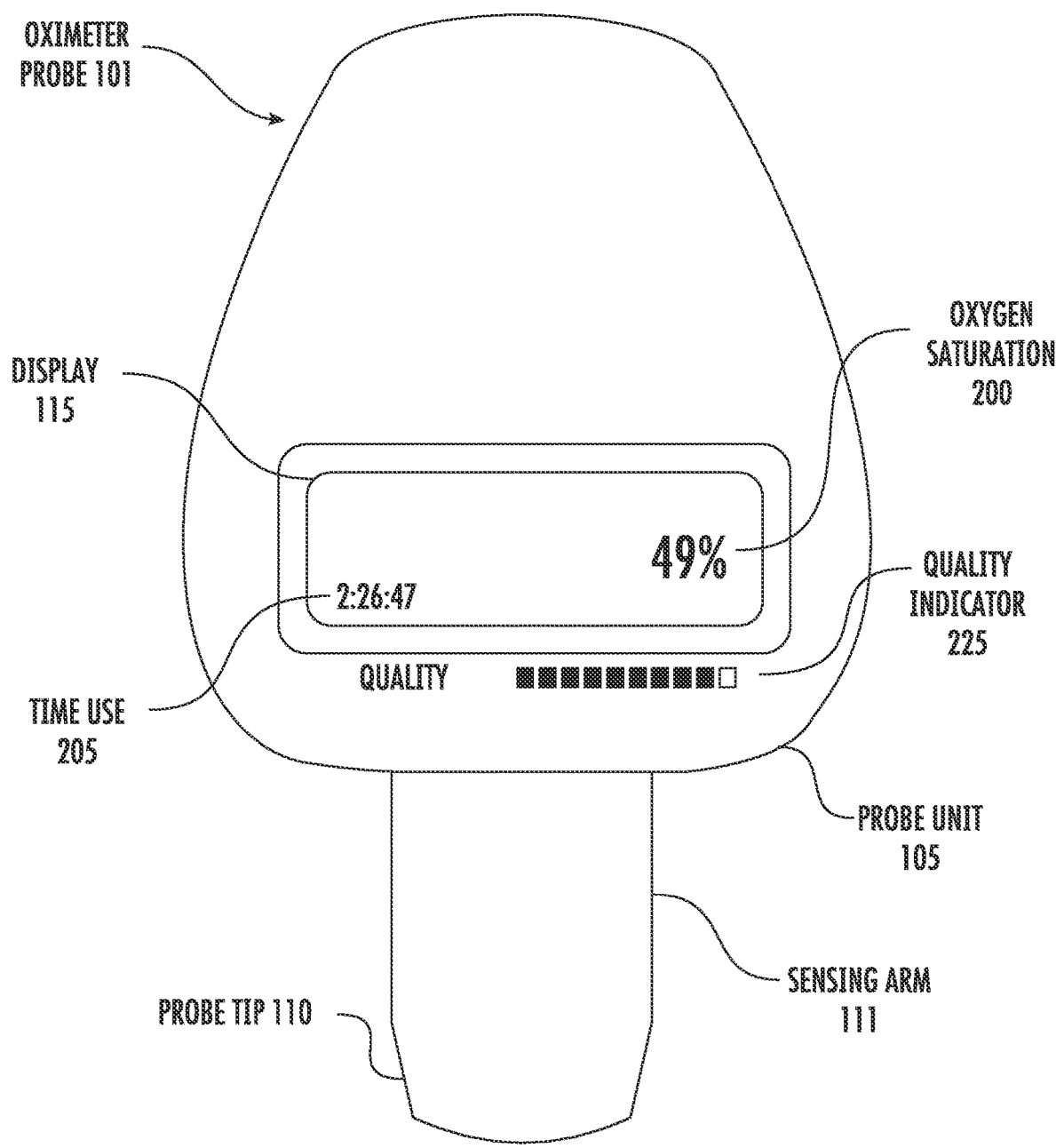
FIG. 4D shows a top view of the oximeter probe in an implementation where the oximeter probe includes a lighted quality indicator.

FIG. 4D shows a top view of the oximeter probe 101 in an implementation where the oximeter probe includes a quality indicator 225. Quality indicator 225 is located in the probe unit in a top portion of the oximeter probe. The quality indicator includes a number of lighting elements that are arranged as a bar graph. The lighting elements are visible from an outer surface of the probe unit, which forms a portion of the mobile housing of the oximeter probe. The lighting elements can include LEDs, organic LEDs (OLEDs), quantum dot LEDs, or other types of lighting elements.

The lighting elements are controlled by the processor to indicate a quality value. Similar to the bar graph of quality indicator 220 described above, the bar graph of quality indicator 225 indicates larger and smaller quality values with larger and smaller number of lighting elements that are lighted.

The bar graph of quality indicator 225 can include 2 bars, 3 bars, 4 bars, 5 bars, 6 bars, 7 bars, 8 bars, 9 bars, 10 bars (FIG. 4D), or more bars. Each bar in the bar graph represents a range of quality values. The ranges represented by the bars can be the same or different. The processor may control and light the bars of quality indicator 225 similar to the control and lighting of the bars of quality indicator 220 described above.

Figure 4E:
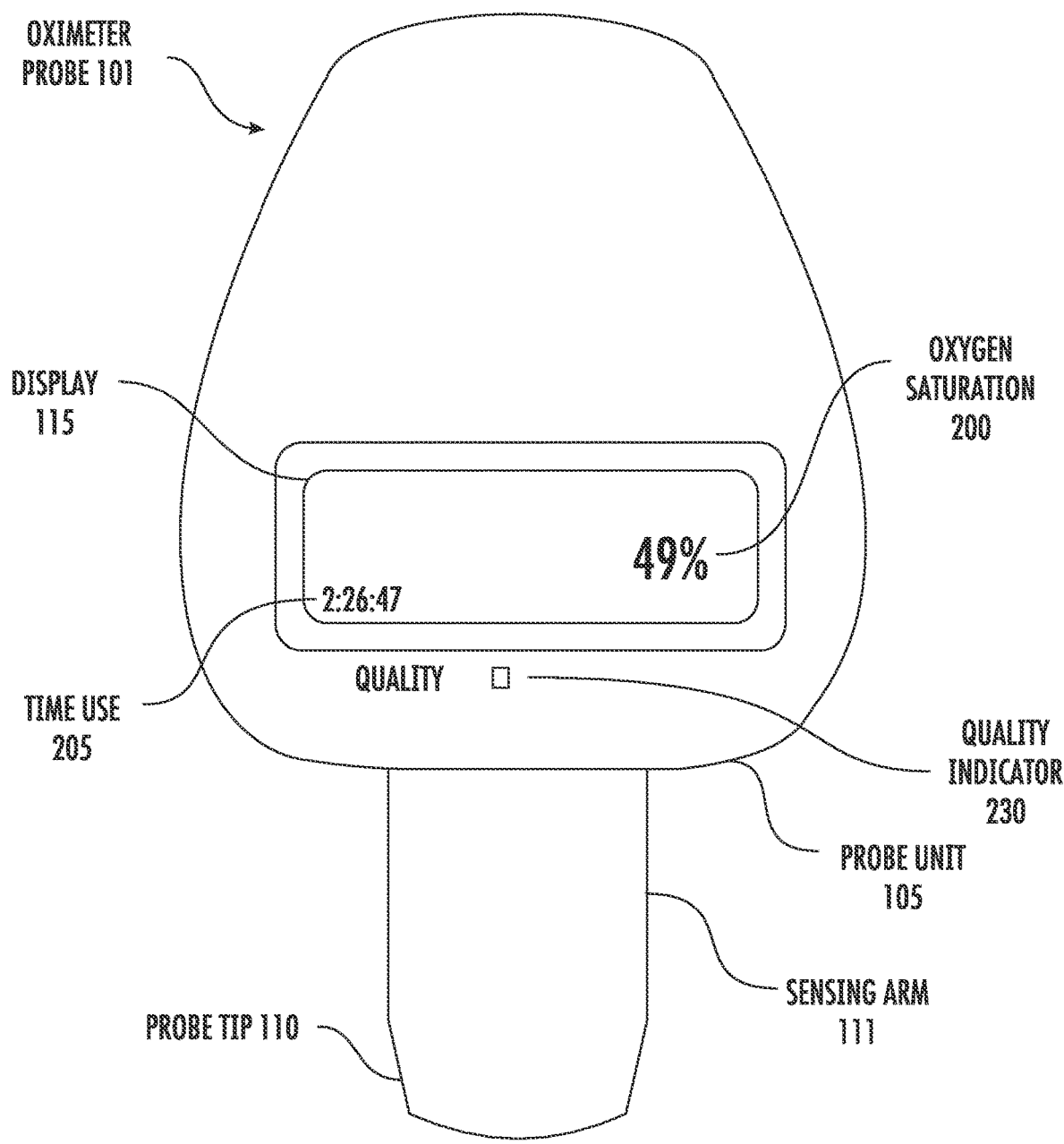
FIG. 4E shows a top view of the oximeter probe in an implementation where the oximeter probe includes a quality indicator that emits different colored light to indicate quality values.

FIG. 4E shows a top view of the oximeter probe 101 in an implementation where the oximeter probe includes a quality indicator 230. Quality indicator 230 is located in the probe unit in a top portion of the oximeter probe. The quality indicator includes a lighting element. The lighting element is visible from an outer surface of the mobile housing of the oximeter probe. The lighting element can include one or more LEDs, organic LEDs (OLEDs), quantum dot LEDs, or other types of lighting elements. The lighting element is adapted to emit a number of visible colors to indicate different quality values. For example, the lighting element can emit 2 colors, 3 colors, 4 colors, 5 colors, 6 colors, 7 colors, 8 colors, 9 colors, 10 colors, or more colors. Each color emitted by the lighting elements indicates a different quality value for the measurement value displayed on the display. In an implementation where the display is a color display, quality indicator 230 can be displayed on the color display.

In an implementation, the lighting element is controlled by the processor to emit a first color of light, such as red, to indicate that the quality value is at or below the threshold quality value (e.g., 70 percent). Alternatively, the lighting element can be controlled not to emit light if the quality value is at or below the threshold quality value. Thereafter, the lighting element can emit different colors of light to indicate different quality ranges. For example, the lighting elements can emit a dark amber color to indicate a quality value of 70 to 80 percent, a light amber color to indicate a quality value of 80 to 90 percent, blue to indicate a quality value of 90 to 95 percent, and green to indicate a quality value of 95 to about 100 percent. The lighting element can emit more or fewer colors for increased range density or decreased range density.

Figure 4F:
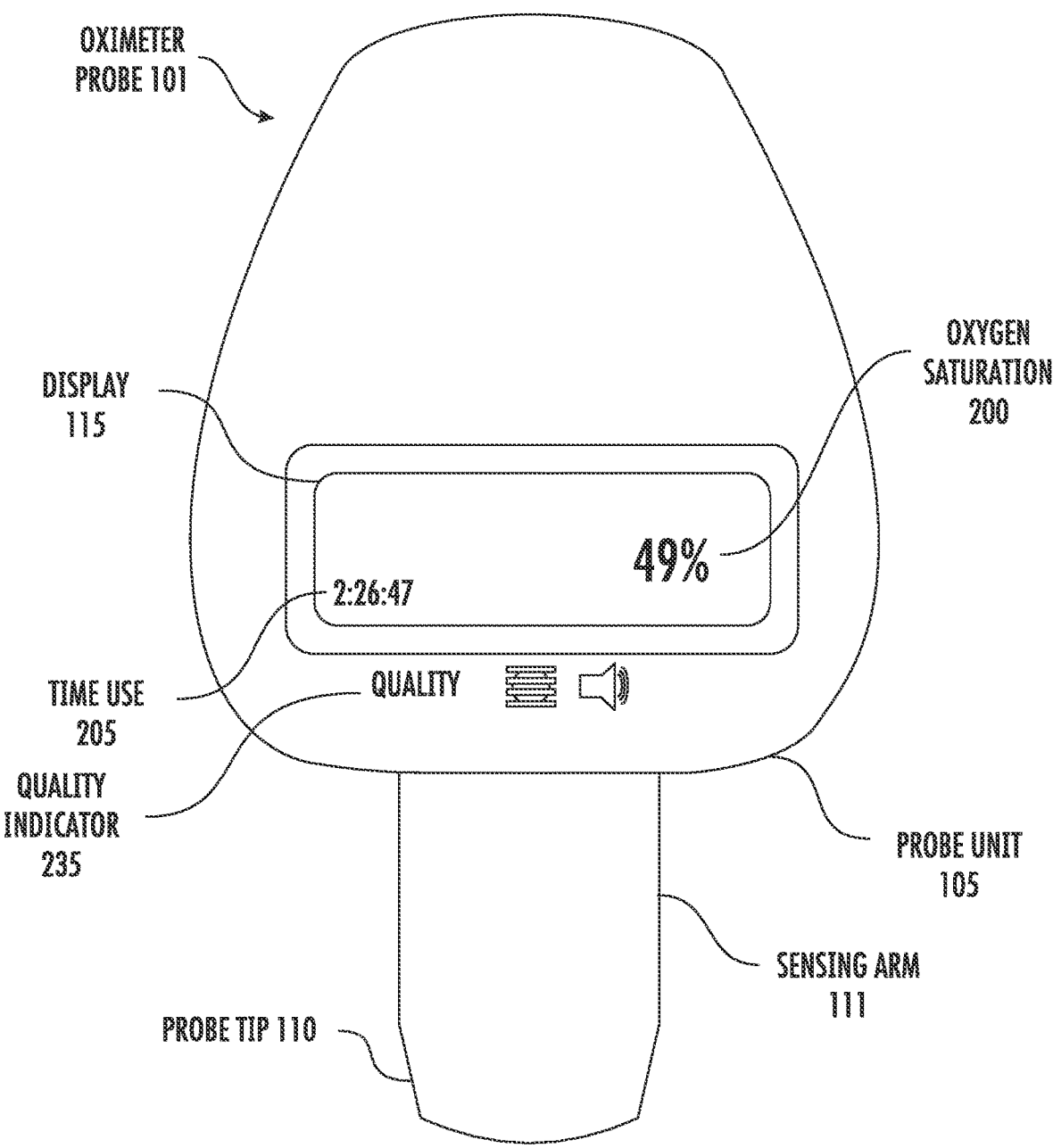
FIG. 4F shows a top view of the oximeter probe in an implementation where the oximeter probe includes a quality indicator that emits various sounds to indicate quality values.

FIG. 4F shows a top view of the oximeter probe 101 in an implementation where the oximeter probe includes a quality indicator 235. Quality indicator 235 is located in the probe unit in a top portion of the oximeter probe. While quality indicator 235, and all other quality indicators described above, is described as being located in the probe unit, the quality indicator can be located in different part of the oximeter probe, such as in the sensing arm 111, in the thumb rest 112.

In an implementation, the quality indicator includes a sound emitting element, such as a speaker or other type of acoustic transducer. The sound emitting element can be located inside the probe unit, such as behind a set of openings (e.g., slots) that allow sound from the sound emitting element to be emitted with little or no obstruction from the unit. Alternatively, the sound emitting element can be coupled to an inside surface of the probe unit where the probe unit does have opening formed in the unit, but where sound passes through the material of the probe unit.

The sound emitting element is coupled to the processor, which controls the conditions for emitting sound from the element and the type of sound that is emitted. For example, the sound emitting element can emit sounds at different frequencies (different sound pitch), can emit sounds, such as clicks sounds, at different frequencies, or can emit different sound volumes. For example, the sound emitting element can emit sound at a first frequency (first pitch) to indicate a first range of quality values (e.g., 0 to 70 percent), emit sound at a second frequency (second pitch) to indicate a second range of quality values (e.g., 70 to 80 percent), emit sound at a third frequency (third pitch) to indicate a third range of quality values (e.g., 80 to 90 percent), and emit sound at a fourth frequency (fourth pitch) to indicate a fourth range of quality values (e.g., 90 to about 100 percent). The first, second, third, and fourth frequencies are different frequencies. The processor can control the sound emitting element to emit more or fewer frequencies to indicate more or fewer ranges of quality.

The processor can control the sound emitting element to emit different frequencies of pulsed sound (e.g., clicks) to indicate the different ranges of quality in a measurement value displayed on the display. The processor can also control the sound emitting element to emit different volumes of sound to indicate the different ranges of quality in a value displayed on the display.

Figure 4G:
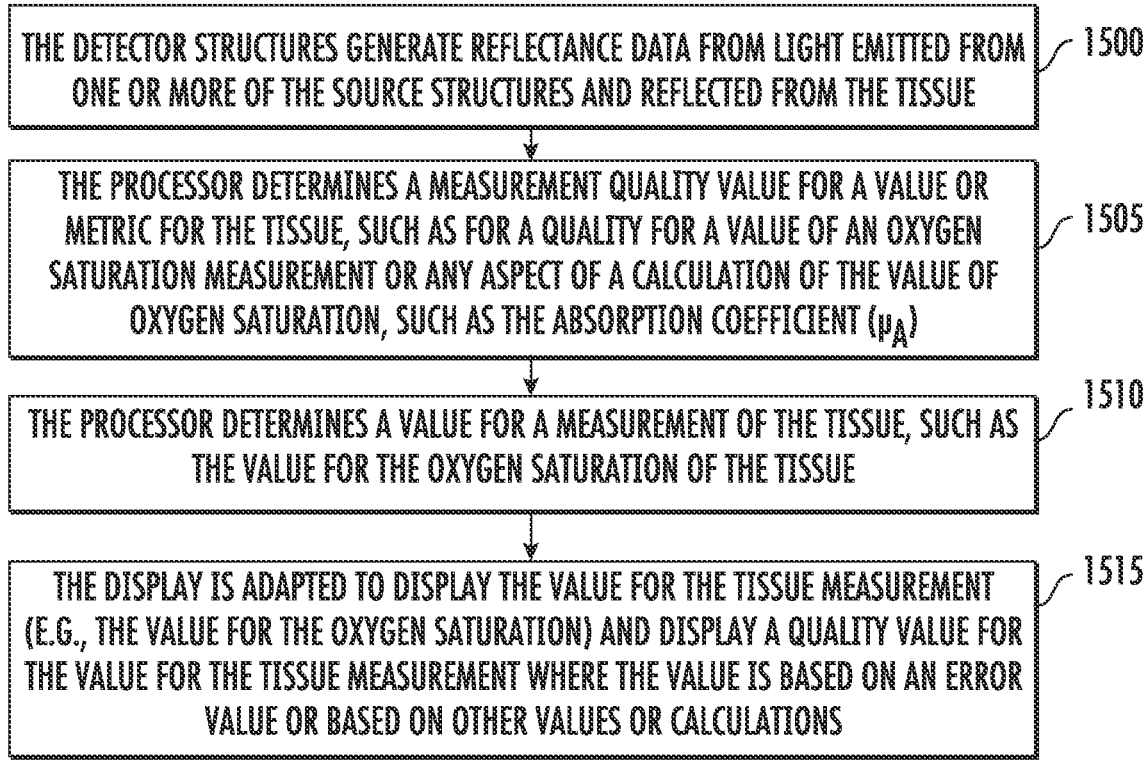
FIG. 4G shows a flow diagram of a method for determining and displaying a quality value on the oximeter probe.

FIG. 4G shows a flow diagram of a method for determining and displaying a quality value on oximeter probe 101 in an implementation. The flow diagram represents one example implementation. Steps may be added to, removed from, or combined in the flow diagram without deviating from the scope of the implementation.

At 1500, the detector structures generate reflectance data from light emitted from one or more of the source structures and reflected from the tissue.

At 1505, the processor determines a measurement quality value for a value for the tissue, such as for a quality for a value of an oxygen saturation measurement or for any aspect or intermediate value of a calculation of the value of oxygen saturation, such as the absorption coefficient ($\mu_a$). The quality value can be calculated by any of the quality value calculations described.

At 1510, the processor determines a value for a measurement of the tissue, such as the value for the oxygen saturation of the tissue.

At 1515, the display is adapted to display the value for the tissue measurement (e.g., the value for the oxygen saturation) and display a quality value for the value for the tissue measurement where the where quality value is based on an error value or based on other values or calculations.

Figure 4H:
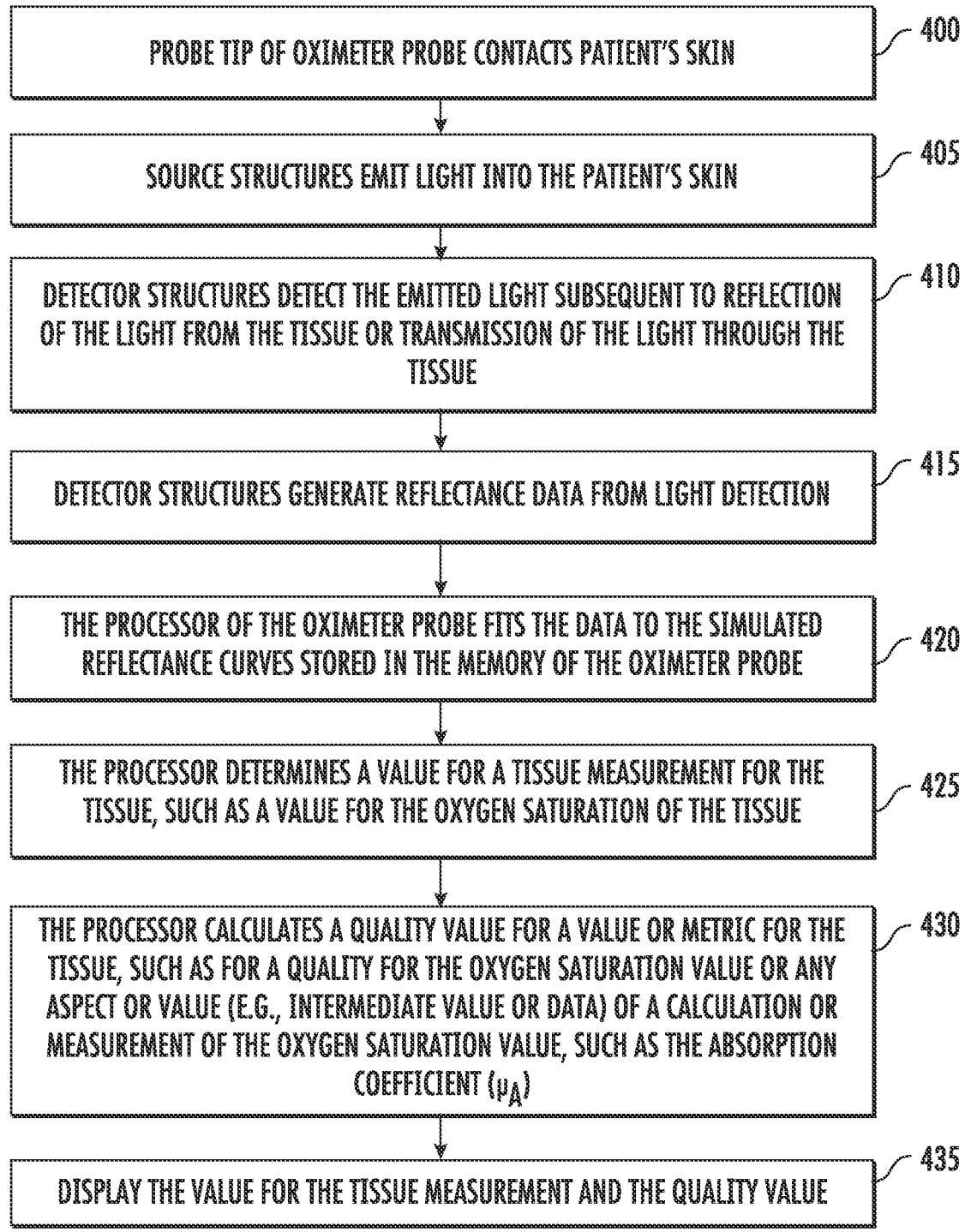
FIG. 4H shows a flow diagram of a method for determining and displaying a quality value on the oximeter probe.

FIG. 4H shows a flow diagram of a method for determining and displaying a quality value on oximeter probe 101 in an implementation. The flow diagram represents one example implementation. Steps may be added to, removed from, or combined in the flow diagram without deviating from the scope of the implementation.

At 400, the probe tip of the oximeter probe contact a patient's tissue, such as the tissue of a human patient. At 405, the source structures of the probe tip emit light (e.g., infrared light) into the tissue. At 410, the light reflects from the tissue and is detected by the detector structures. At 415, the detector structures generate reflectance data from the detected light. At 420, the processor fits the reflectance data to simulated reflectance curves 315 stored in the memory of the oximeter probe to determine a best fit of the reflectance data to the curves.

At 425, the processor determines one or more measurement values of the tissue, such as a value for oxygen saturation, a value for blood volume, a value for the melanin concentration, or other measurement values based on the fit of the reflectance data to the simulated reflectance curves.

At 430, the processor calculates a quality value for a value for the tissue, such as for a quality for a value of an oxygen saturation measurement or any aspect of a calculation of the value of oxygen saturation, such as the absorption coefficient ($\mu_a$). The quality value can be determined by the processor via comparison and assessment of the relationship between the reflectance at the detector structures and the reflectance data generated by the detector structures. This relationship can be based on raw data generated by the detector structures, filtered data, calibrated data, analog-to-digital converter (ADC) counts, or any other manipulation of the data. The quality value may be calculated by the processor based on relationships between two or more detectors and one or more sources. The quality value may be calculated based on detector data from one source location (e.g., source structure 120a) versus another source location (e.g., source structure 120b).

In an implementation, the quality value is determined by comparing relationships between measurements, predictions, or both made at similar times. The measurements for the similar times can be for time points during a temporal series of oximeter measurements (e.g., three, four, five, six, or more oximeter measurements over a period of time when the measurements are made on tissue of a patient) where the measurements for the similar times are compared to each other. A particular oximeter measurement can be made in a number of microsecond, a number of milliseconds, or smaller or longer periods. The series of oximeter measurements can be for predictions of tissue parameters, such as values for oxygen saturation, values for relative oxygen saturation, or any calculated valued used by the oximeter probe for calculating a subsequent value, such as where the subsequent value is an oxygen saturation value or a relative oxygen saturation value on particular patient tissue) to one another. Noise in the oximeter measurements (e.g., formalized as a coefficient of variance in absorption predicted at a particular wavelength over the course of three oximeter measurements) is used by the oximeter device to adjust a first quality metric (e.g., that is based on an error versus the curve).

The quality value determined by the processor can be based on ratiometric calculations or ascertained by comparing data distributions (e.g., through methods similar to the Bhattacharyya or Mahalanobis distance). The quality value may also be calculated by the processor based on the current relationship among detectors compared with typical relationships among the detectors which are stored in memory 117. The quality value can be an error value for the fit of the reflectance data to one or more reflectance curves that best fit the data. The error value can be determined from one or more of a number of error fitting techniques, such as a least squares technique, a weighted least squares technique, a regularization technique, such as the Tikhonov regularization technique, the Lasso technique, or other techniques. The quality value can be the error value or can be derived from the error value. A "best" fitting or "closest" fitting simulated reflectance curve to reflectance data for a tissue measurement can be a simulated reflectance curve that has a smallest error value determined from one of the error fitting techniques or other error fitting techniques.

As described, a quality value for a given displayed value may be determined or calculated by one or more different techniques, or a combination of these. As an example, the quality value shown on the display may be a moving average value of multiple measurement samples of oxygen saturation or other values, intermediary values, aspects, calculations, intermediary calculations, or measurements used in determining a measured value, such as the oxygen saturation. The quality value gives an indication of how close the distribution (e.g., standard deviation or variance) of measured samples is to the moving average. The more closely the sampled measurements are grouped together and are close to the moving average, this indicates a higher quality measurement. In contrast, the less tightly spaced the samples are, the less quality of the measurement.

For example, in a first case, a first measurement is based on a distribution curve where one standard deviation is, for example, X percent from the average. In a second case, a second measurement is based on a distribution curve where one standard deviation is, for example, Y percent from the average. Y is greater than X. Then, when displaying the first measurement, the quality indicator will show a higher value than when displaying the second measurement.

At 435, the processor controls the display to display the value for the measurement value (e.g., oxygen saturation value) and control the presentation of quality value for the displayed value. The quality values can be presented on the display as a percentage (e.g., quality indicator 210, FIG. 4A), via a bar graph displayed on the display (e.g., bar graph 220, FIGS. 4B-4C), via lighted bar graph (e.g., quality indicator 225, FIG. 4D), via a color light emitting quality indicator (e.g., quality indicator 230, FIG. 4E), via a sound emitting quality indicator (e.g., quality indicator 235, FIG. 4f), or via other quality indicator.

Figure 4I:
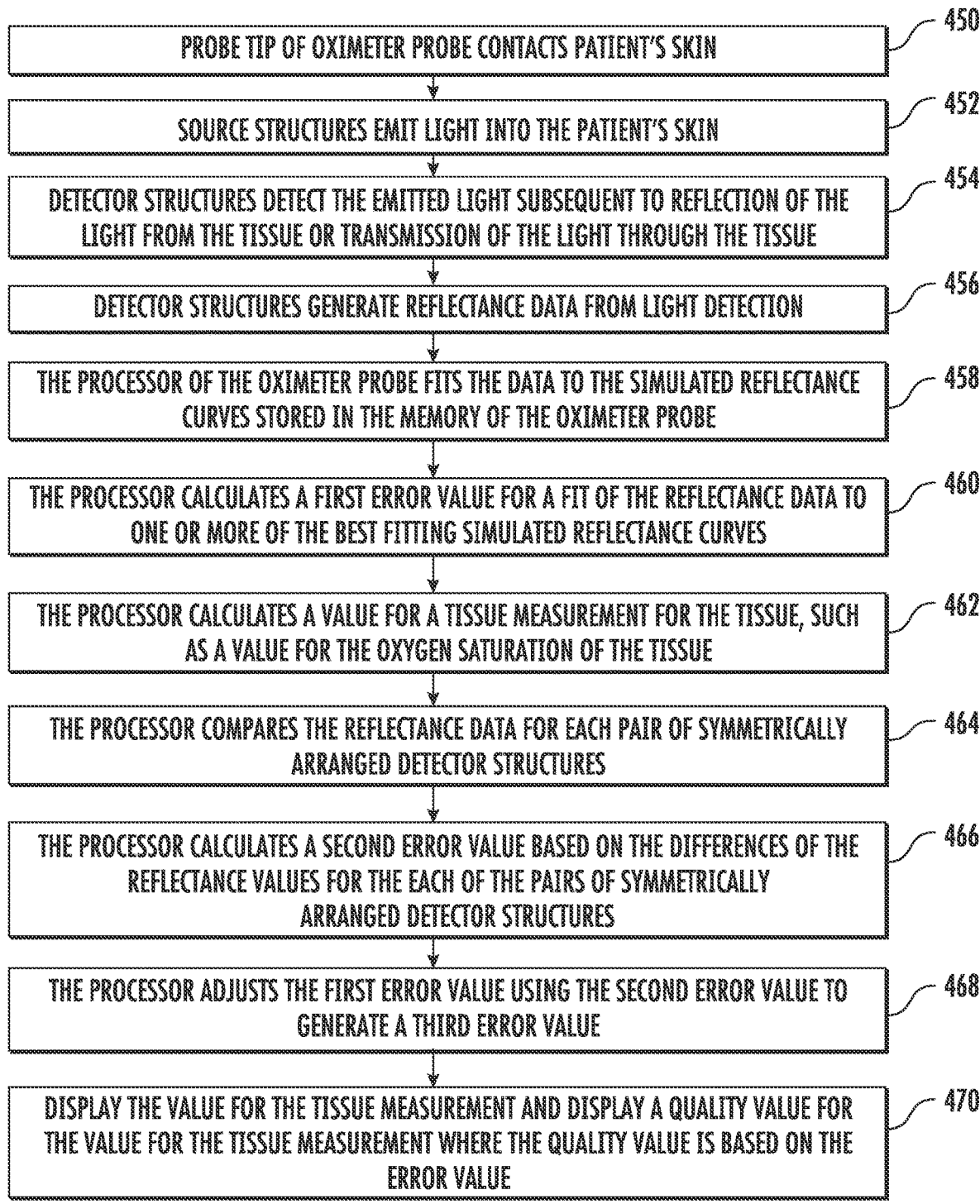
FIG. 4I shows a flow diagram of a method for determining inhomogeneity in oximeter measurements for pairs of symmetrically positioned detector structures.

FIG. 4I shows a flow diagram of a method for determining inhomogeneity in oximeter measurements in an implementation. The flow diagram represents one example implementation. Steps may be added to, removed from, or combined in the flow diagram without deviating from the scope of the implementation.

At 450, the probe tip of the oximeter probe contact a patient's tissue, such as the tissue of a human patient. At 452, the source structures of the probe tip emit light (e.g., infrared light) into the tissue. At 454, the light reflects from the tissue and is detected by the detector structures. At 456, the detector structures generate reflectance data from the detected light. At 458, the processor fits the reflectance data to simulated reflectance curves 375 stored in the memory of the oximeter probe to determine a best fit of the reflectance data to the curves.

At 460, the processor calculates a first error value for the fit of the reflectance data to one or more reflectance curves that best fit the data. The error value can be determined from one or more of a number of error fitting techniques, such as a least squares technique, a weighted least squares technique, a regularization technique, such as the Tikhonov regularization technique, the Lasso technique, or other techniques.

At 462, the processor determines one or more tissue measurement values of the tissue, such as the oxygen saturation, the blood volume, the melanin concentration, or other tissue measurement values based on the fit of the reflectance data to the simulated reflectance curves.

At 464, the processor compares reflectance data for detector structures that are symmetrically located with respect to each other about a point on a line connecting source structures 120 and 120b. For example, in an implementation, detector structures 125a and 125e are symmetrically positioned about a point on a straight line connecting source structures 120a and 120b. Detector structures 125b and 125f are symmetrically positioned about the point. Detector structures 125c and 125g are symmetrically positioned about the point. Detector structures 125d and 125h are symmetrically positioned about the point. As described above with respect to FIG. 2, the point can be centered between source structures 120a and 120b on the connecting line.

More specifically, at step 464, the processor compares reflectance data generated by detector structures 125a and 125e, compares reflectance data generated by detector structures 125b and 125, compares reflectance data generated by detector structures 125c and 125g, and compares reflectance data generated by detector structures 125d and 125h.

At 466, if the magnitudes of the reflectance data for two symmetrically positioned detector structures differ by a threshold reflectance amount or more, then the processor generates a second error value based on the difference in the reflectance data. The reflectance data might differ for two symmetrically positioned detector structures if the pressure applied to the probe type is not uniform across the face of the probe tip and the detector structures are positioned different distances away from the surface of the tissue as a result of the nonuniformly applied pressure. Difference in reflectance data can also occur for skin having varying skin color, such as skin with freckles or vitiligo.

At 468, the processor adjusts the first error value using the second error value to generate a third error value. The first error value can be adjusted by the second error value via one or more of a variety of techniques including one or more arithmetic corrections, a functional correction, both of these corrections, or other corrections.

In some implementations, the first error value can be relatively high for skin that is relatively light or relatively dark. The tissue measurements (oxygen saturation measurements) made by the oximeter probe for skin having these relatively light and dark skin colors can be more accurate than indicated by the first error value. Therefore, the adjustment to the first error value using the second error value can be applied by the processor for skin having these relatively light and dark colors. Determination of skin color is described below.

At 470, the processor controls the display to display the measurement value for the tissue parameter (e.g., oxygen saturation value) and control the presentation of quality value for the displayed value. The quality value can be the third error value or can be derived from the third error value. The quality values can be presented on the display as a percentage (e.g., quality indicator 210, FIG. 4A), via a bar graph displayed on the display (e.g., bar graph 220, FIGS. 4B-4C), via lighted bar graph (e.g., quality indicator 225, FIG. 4D), via a color light emitting quality indicator (e.g., quality indicator 230, FIG. 4E), via a sound emitting quality indicator (e.g., quality indicator 235, FIG. 4f), or via other quality indicator.

Figure 4J:
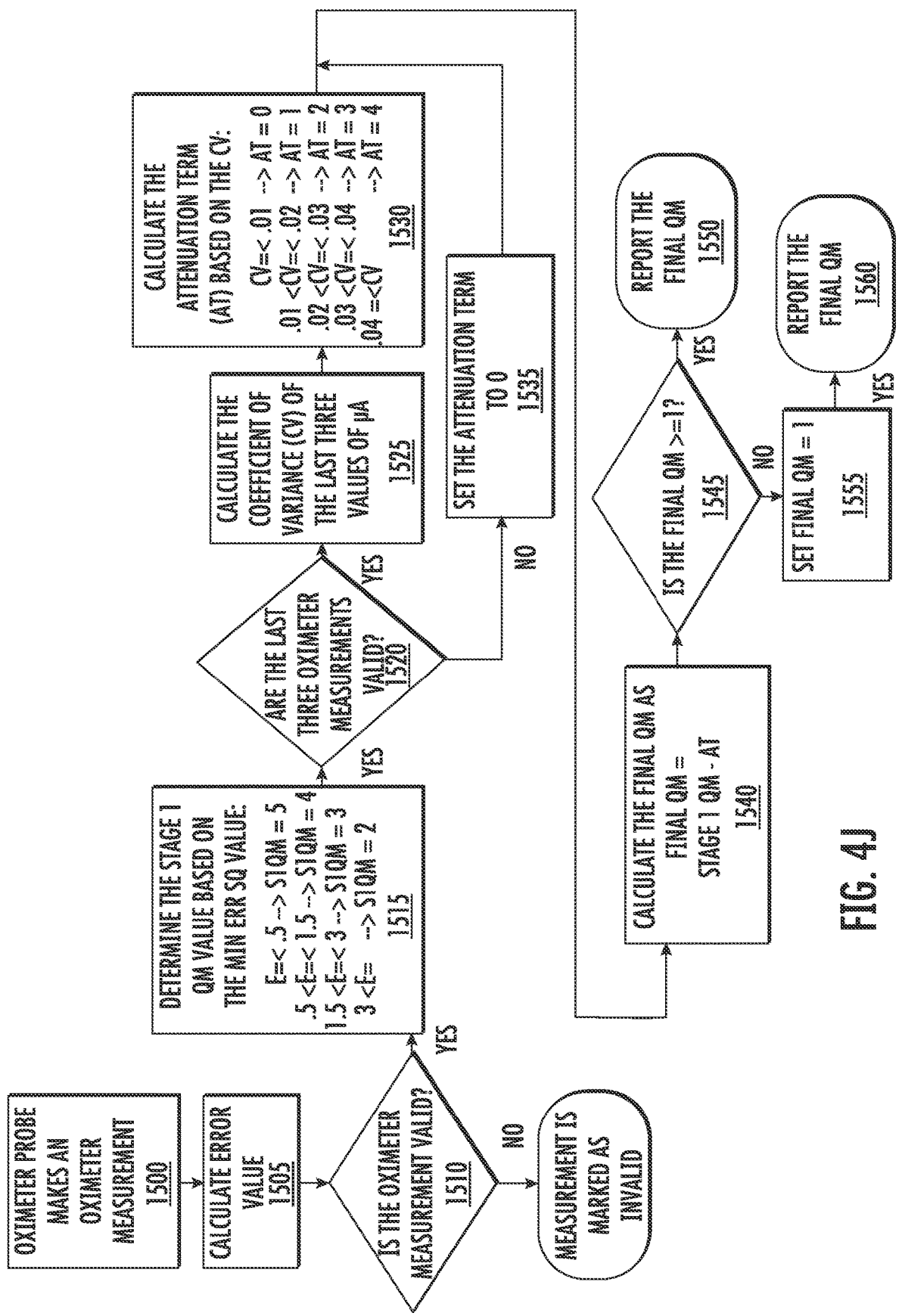
FIG. 4J shows a flow diagram of a method for determining a quality metric for oximeter measurements.

FIG. 4J shows a flow diagram of a method for determining a value for a quality measure (e.g., quality value) that indicates a degree of certainty of displayed oximetry measurements. The quality metric informs a user of the oximeter device whether the displayed values for oximetry measurements are accurate. The flow diagram represents one example implementation. Steps may be added to, removed from, or combined in the flow diagram without deviating from the scope of the implementation.

The method facilitates the display of an on-screen quality measure value in the range from 0-10, or other range, to indicate the quality of displayed oximetry measurements to thereby aid users in determining whether the displayed oximeter measurements are acceptable and reliable.

More specifically, the quality metric provides an indication of the consistency of light detected between select detectors of pairs of detectors of the oximetry probe. As described above, a number of pairs of detector include the first and second detectors that are equidistant from the first and second sources, respectively. In the example of FIG. 2 and table 1, D4 and D8 are equally distant from S1 and S2, respectively, as are other pairs of detectors with respect to the first and second sources S1 and S2. Higher equality of light detected by two detectors that are equidistant form the sources are described as having higher quality values and lower equality of light detected by the two detectors are described as having lower quality values.

The loss of light in tissue being measured should be equal at first and second detectors of a pair of detectors that are equidistance from the first and second sources, respectively Deviation from detection of equal loss of light from tissue can indicate one or more modes (e.g., two modes) of loss of light from equality. A first mode of deviation from equality is associated with one of the first and second detectors being above the tissue surface or the two detectors being placed on the tissue surface with different pressure.

Figure 4K:
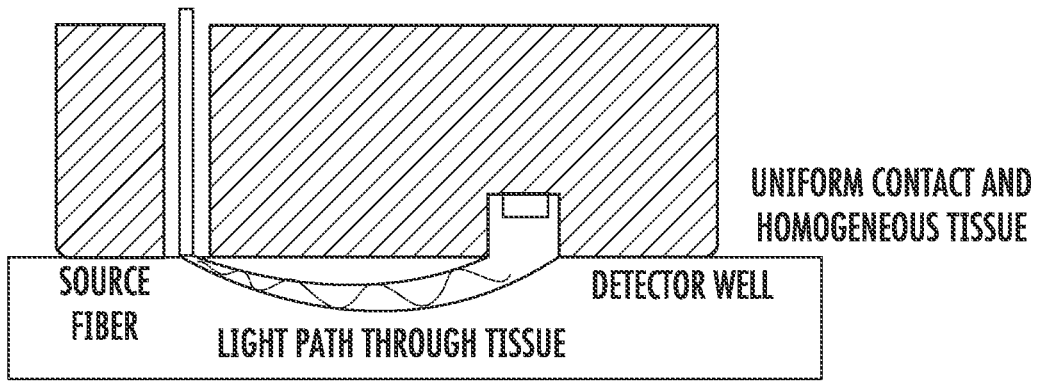
FIGS. 4K and 4L show first and second detectors where one of the detectors is in contact with the tissue and the second detector is above the surface of the tissue.
Figure 4L:
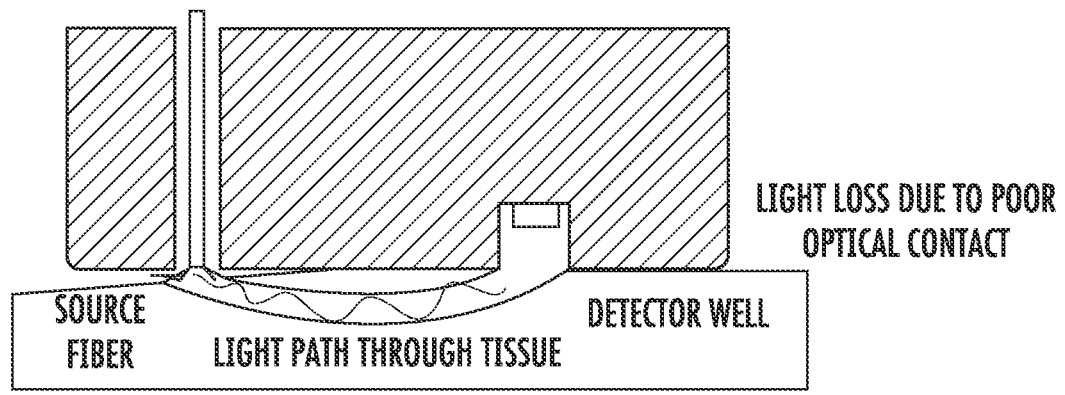

FIGS. 4K and 4L show first and second detectors where one of the detectors is in contact with the tissue and the second detector is above the surface of the tissue. The first and second detectors are equidistant from the first and second sources, respectively.

Figure 4M:
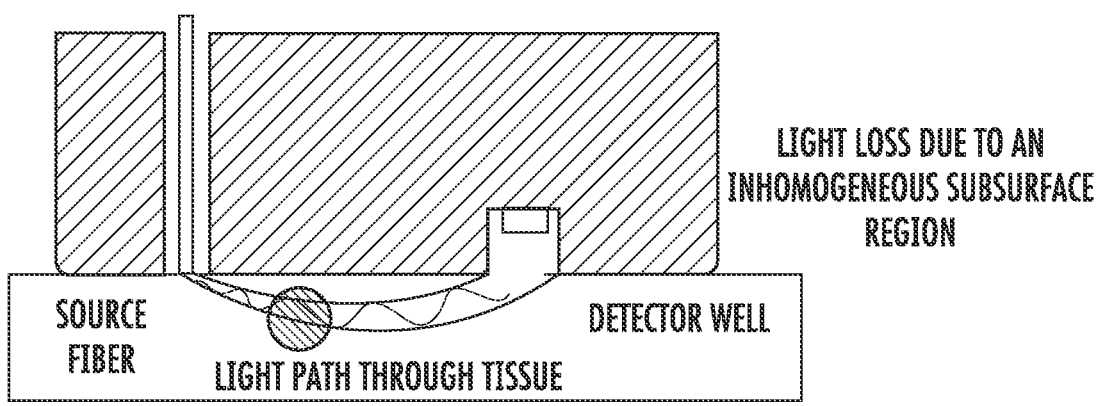
FIG. 4M shows tissue having an inhomogeneous portion of tissue as compared to surrounding tissue.
Figure 4N:
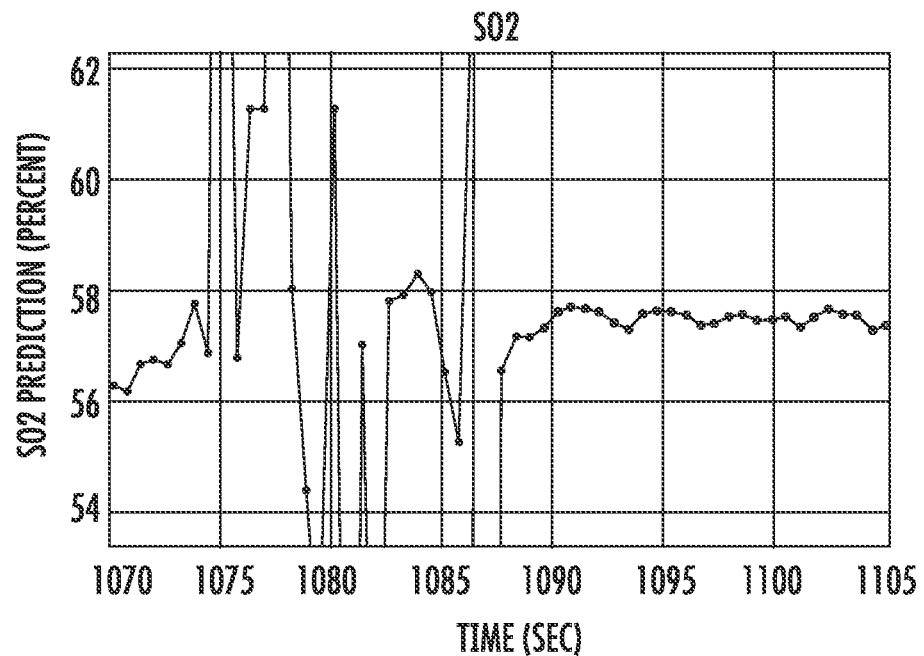
FIGS. 4N-4Q show graphs of oximeter measurements for StO2, the Minerrrsq value (described below), mua, and mua prime.
Figure 4O:
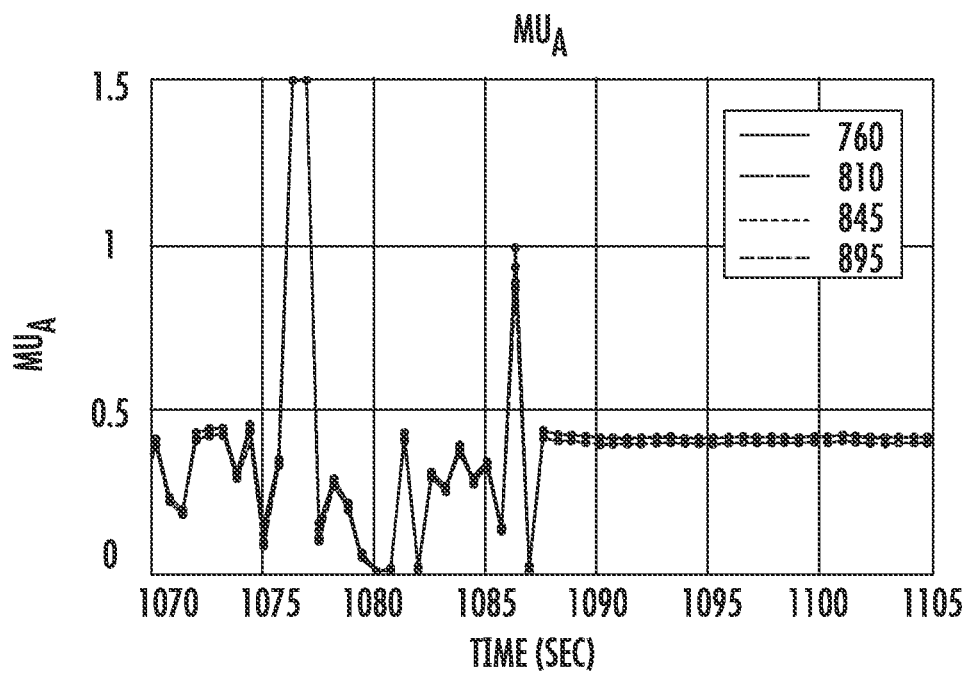
Figure 4P:
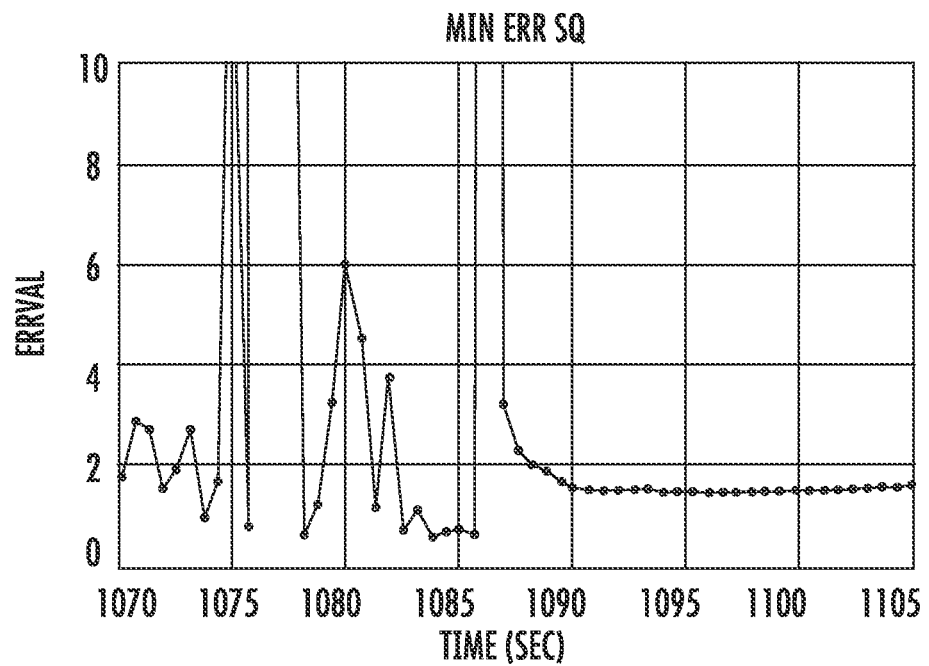
Figure 4Q:
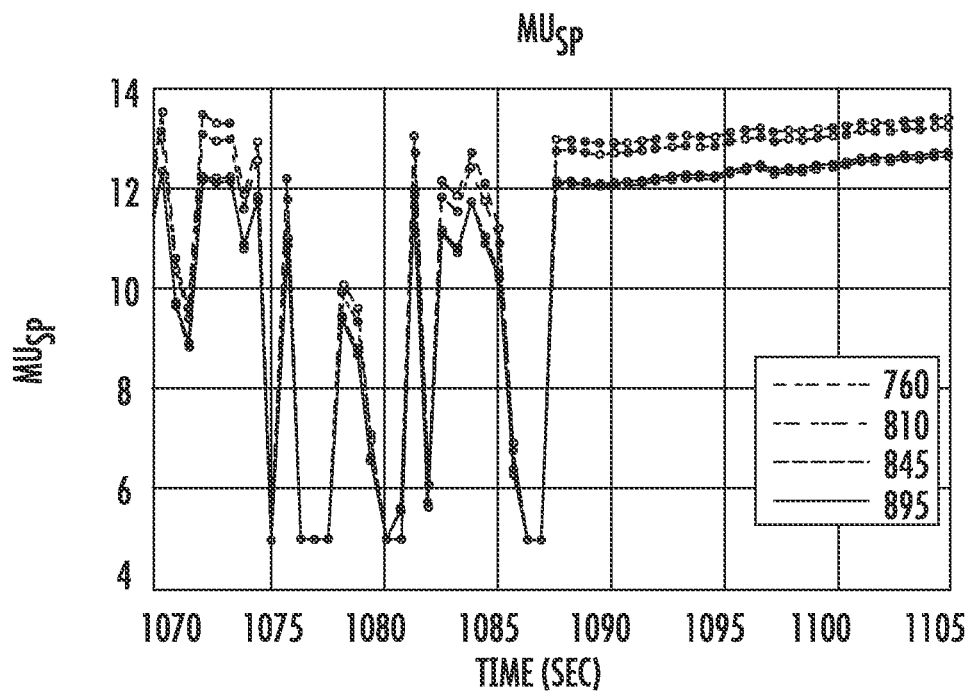

A second mode of deviation from equality of light detection by the first and second detectors is associated with an inhomogeneity in the subsurface region of the tissue. Specifically, between two light paths between the first detector and the first source (first light path) and between the second detector and the second source (second light path) where the paths are equidistant, the inhomogeneity is in one of the two light paths. FIGS. 4K and 4M show the two light paths with an inhomogeneity of tissue region along the light path of FIG. 4M.

The quality measure is calculated by two steps as further described below. In a first step, a "stage 1" quality measure (QM) is determined based the error values. Low error values correspond to high stage 1 QM values, whereas higher error values (e.g., lower than the low error values) correspond to lower stage 1 QM values (e.g., lower than the high stage 1 QM values).

In a second step, an adjustment for the stage 1 QM values is determined. The adjustment for the stage 1 QM in the second step is based on an artifact created in the first step associated with noise associated with unstable contact (i.e., movement) of the probe tip for a conditioned favored by the first step where the probe tip is positioned 1 millimeter or approximately 1 millimeters above the tissue surface.

FIGS. 4N-4Q show graphs of oximeter measurements for StO2, the Minerrrsq value (described below), mua, and mua prime. The approximate left half of each graph show the parameters for unstable contact between the probe face and tissue and the approximate right half of the graphs show the parameters for stable contact. The first and second steps are presently further described.

At 1500, the oximeter probe makes an oximeter measurement when the oximeter probe being is contacted to a patient's tissue, such as the tissue of a human patient. The source structures of the probe tip emit light (e.g., infrared light) into the tissue. The light reflects from the tissue and is detected by the detector structures. The detector structures generate reflectance data from the detected light. The processor fits the reflectance data to simulated reflectance curves 375 stored in the memory of the oximeter probe to determine a best fitting one or more of the simulated reflectance curves to the reflectance data. A best fitting simulated reflectance curve to the data can be a fit that has a lowest error value determined by a fitting algorithm, such as a minimum error square, a least squares technique, a weighted least squares technique, a regularization technique, such as the Tikhonov regularization technique, the Lasso technique, or other techniques.

At 1505, the processor calculates the error value for the fit of the reflectance data to one or more reflectance curves that best fit the data. In an implementation where a minimum error square techniques is used, the error value is a minimum error square value ("MinErrSq" value).

At 1510, the processor compares the error value to an error threshold hold value to determine whether the oximeter measurement is valid. If the error value is less than the error threshold value, then the oximeter measurement is valid. If the error value is equal to or greater than the error threshold value, then the oximeter measurement is not valid.

If the oximeter measurement is determined to be valid, then the error value (e.g., the MinErrSq value) is mapped (e.g., converted) from a range of errors values in which the error values lies to a value that represents the range. See 1515 in FIG. 4J. The values that represent ranges of error values are referred to as stage 1 quality measure (QM) values. In an implementation, the MinErrSq values are whole numbers or fractional values and the stage 1 QM values are integers.

The mapping can be determined from a lookup table, can be calculated from the error values, or otherwise determined. Table 2 below shows an example lookup table that might be used for converting the MinErrSq values to the stage 1 QM values.

TABLE 2

| Equality Relationship of MinErrSq Value | Stage 1 Quality Measure (QM) |
|---|---|
| First range of error values: MinErrSq value is less than or equal to 0.5; (value < or = 0.5) | 5 |
| Second range of error values: If MinErrSq value is greater than 0.5 and less than or equal to 1.5 (e.g., 0.5 < value <= 1.5) | 4 |
| Third range of error values: If MinErrSq value is greater than 1.5 and less than or equal to 3.5 (e.g., 1.5 < value <= 3) | 3 |
| Fourth range of error values: If MinErrSq value is greater than 1.5 and less than or equal to 3.5 (e.g., value < 3) | 2 |

Table 2 shows that the four ranges of error values are mapped to four integer stage 1 QM values. In other implementations, more or fewer ranges and stage 1 QM values are used. Further, the width of the ranges of the MinErrSq values are different (e.g., wider ranges or narrower ranges) in other implementations. Further, the integer values (e.g., 2, 3, 4, and 5) are different in other implementations.

The stage 1 QM values are quality measure values that incorporate error effects from (i) uneven contact of the probe face of the oximeter probe with the tissue, (ii) asymmetric pressure of the probe face on the tissue, and (iii) local inhomogeneity of the tissue.

At 1520, the processor determines whether a number (e.g., 3 or other number of prior oximeter measurements) of the prior oximeter measurements are valid or not valid. The number of other oximeter measurements can be measurement made prior to the current oximeter measurement being described, can includes the current oximeter measurement being described, can be oximeter measurements made before and after the current oximeter measurement being described, or can be oximeter measurements made after the current oximeter measurement being described.

If the number (e.g., 3) of the prior oximeter measurements are valid, then the processor calculates a coefficient of variance value for the last numbers (e.g., 3) of absorption coefficients values for the last numbers (e.g., 3) oximeter measurements for a particular wavelength transmitted by the source structures of the oximeter probe. In an implementation, the wavelength is 859 nanometers. The coefficient of variance value can be the standard deviation divided by the mean for the $\mu_a$ values for 895 nanometers.

The coefficient of variance value can be calculated according to:

$CV = (\Sigma(\mu_a - \text{average}(\mu_a))/(n-1))^{1/2}/\text{average}(\mu_a)$. The average $\mu_a$ can be for the last number (e.g., 3) of $\mu_a$ for the last number of oximeter measurements. See 1525 of FIG. 4J.

The CV value is thereafter converted into an attenuation term (AT) value. The CV value can be converted into the AT value via lookup table (e.g., database) that stores the conversion information. Table 3 below is an example lookup table used for converting the CV value into the AT value. See 1530 of FIG. 4J.

TABLE 3

| Coefficient of Variance Values | Attenuation Term Values |
| --- | --- |
| First range of CV values: CV value is less than or equal to 0.01; (value < or = 0.01) | 0 |
| Second range of CV values: If CV value is greater than 0.01 and less than or equal to 0.02 (e.g., 0.01 < value <= 0.02) | 1 |
| Third range of CV values: If CV value is greater than 0.02 and less than or equal to 0.03 (e.g., 0.02 < value <= 0.03) | 2 |
| Fourth range of CV values: If CV value is greater than 0.03 and less than or equal to 0.04 (e.g., 0.03 < value <= 0.04) | 3 |
| Fifth range of CV values: If CV value is greater than 0.04 (e.g., value < 0.04) | 4 |

If the number of the prior oximeter measurements are not valid, then the processor of the oximeter device, sets the AT value to zero. See 1535 of FIG. 4J. In an alternative implementation, if the number of the prior oximeter measurements are not valid, then the processor of the oximeter device, the oximeter device displays the value for the stage 1 QM on the display. For example, the stage 1 QM value 2, 3, 4, or 5 (or others if other numbers are used) is displayed on the display based on the MinErrSq value.

At 1540, the processor calculates a further quality measure (QM), which can be a final QM. The final QM can be calculated as: final QM=Stage 1 QM−AT.

If the processor determines that the final QM value is greater than or equal to 1 (e.g., final QM>=1), then the calculated final QM value is displayed on the display. See 1545 and 1550 in FIG. 4J.

If the processor determines that the final QM value is not greater than or equal to 1, then the final QM value set to 1, and this final QM value 1 is displayed on the display. See 1555 and 1560 in FIG. 4J. When the final QM is not greater or equal to 1, a possibility exists that the AT value is greater than the final QM value, and the determination of final QM=Stage 1 QM−AT can yield a negative value for the final QM. Rather than report a negative value for final QM, the final QM is set to 1 at 1555.

In an implementation, the speaker emits one or more audible indicators to indicate the final QM value or other QM values described in this patent. The audible indicators can be different tones, spoken words, or others.

In an implementation, the oximeter probe produces haptic feedback, such as one or more vibrations, clicks or other indicator to indicate the final QM or other QM values described in this patent. The haptic feedback can include one or more clicks or pulses to indicate the integer values determined for the final QM.

In an implementation, the button or other input device on the oximeter probe can be pressed to scroll the display to display StO2 values and then the QM values and then the TtO2 values in a repeating (e.g., scrolling) manner. Two or more pieces of oximetry information (e.g., StO2 and QM values) can be display on the same time.

In an implementation, the button or other input device on the oximeter probe can be pressed to display to the final QM value or other QM values described in this patent. The QM values may not be displayed until the button is pressed, and the display of the QM values may switch back to display of the StO2 value when the button is no longer pressed. A displayed QM value displayed on the display can be the QM value for a previous (e.g., immediately previous) displayed StO2 value.

In an implementation, the button or other input device on the oximeter probe can be pressed to scroll the display of calculated QM values, such as for a first tissue location and a second tissue location, or for first and second oximeter measurements.

In an implementation, the display switching between display of the StO2 value and the QM value based on a time period, such as 1 second, 2 seconds, 3 seconds, 4 seconds, 5 seconds, or other temporal lengths. That is, when the StO2 value is displayed on the display, the QM value is not displayed on the display at the same time as the StO2 value, and the when the QM value is displayed on the display, the StO2 value is not displayed on the display at the same time as the QM value. A displayed QM value displayed on the display can be the QM value for a previous (e.g., immediately previous) displayed StO2 value.

In an implementation were different types of values (e.g., StO2 and QM) are displayed on the display, text is displayed that indicates the type of information being displayed.

Figure 4R:
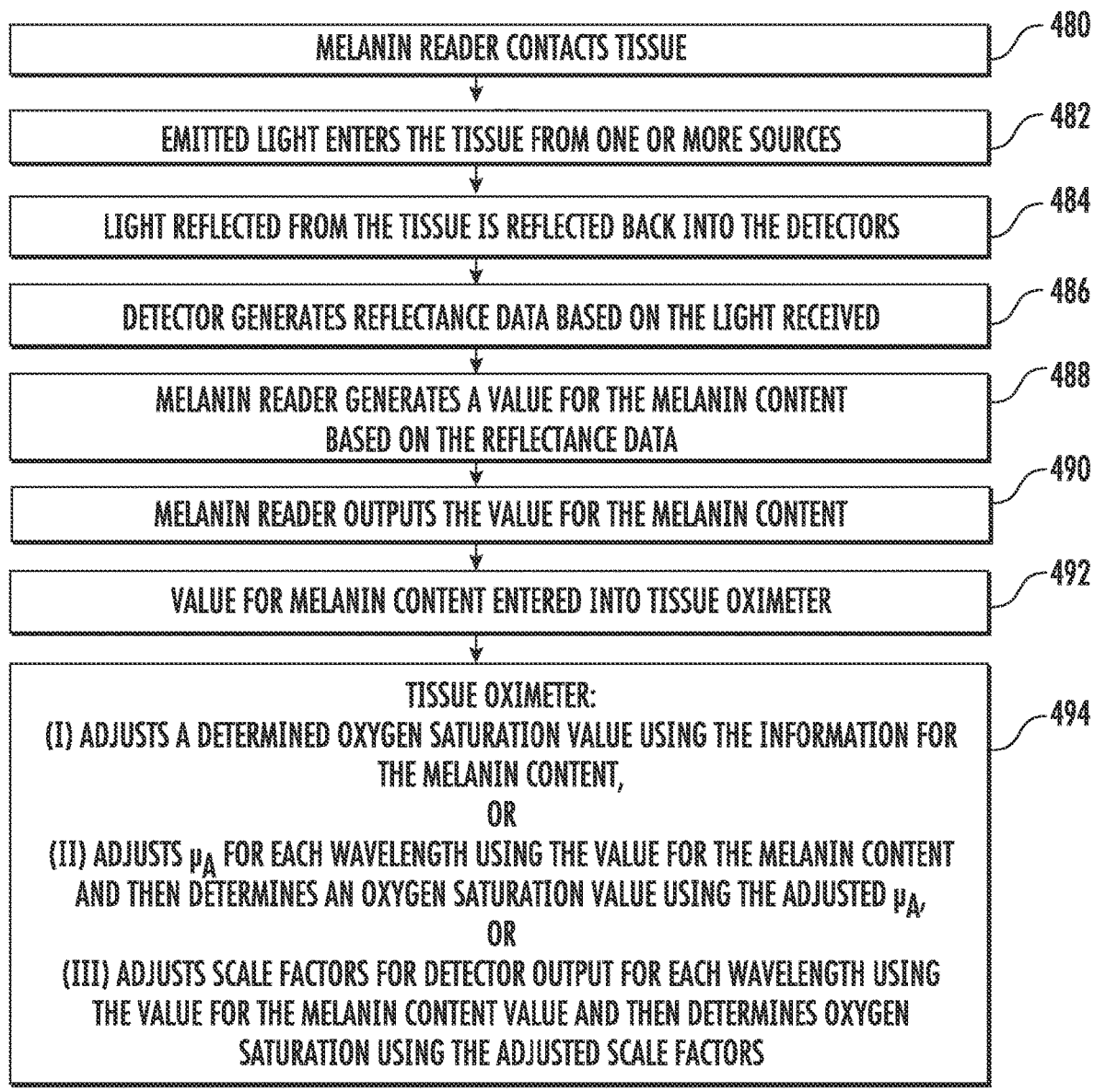
FIG. 4R shows a flow diagram of a method for determining optical properties of tissue by the oximeter probe.

Tissue Analysis. FIG. 4R shows a flow diagram of a method for determining optical properties of tissue (e.g., real tissue) by oximeter probe 101 in an implementation. The oximeter probe uses determined melanin content for the tissue to correct various tissue parameters that are measured by the oximeter probe. The flow diagram represents one example implementation. Steps may be added to, removed from, or combined in the flow diagram without deviating from the scope of the implementation.

At 480, a melanin reader optically couples (e.g., contacts) to the tissue. Melanin readers are optoelectronic devices that are adapted for emitting light, step 482, into tissue, and detecting the light, step 484, after having been transmitted through the tissue or reflected from the tissue. The light detected by the melanin reader is converted to electrical signals, step 486, that are used by the device to determine melanin content of the tissue, step 488. The melanin reader can output a value for the melanin content, step 490, on a display of the reader or via a wired or wireless output.

In an implementation, at 492, information (e.g., a numerical value) about the melanin content is entered into oximeter probe 101. The information can be entered into the oximeter probe via a user (e.g., a human user) or via a wired or wireless communication between the melanin reader and the oximeter probe.

In a first implementation, at 494, the oximeter probe uses the information for the melanin content to adjust one or more measured values generated by the probe. In an implementation, the oximeter probe determines a value for the oxygen saturation of the tissue. The oximeter probe thereafter adjusts the value for the oxygen saturation using the information for the melanin content. The oximeter probe can adjust the value for the oxygen saturation via one or more arithmetic operations, mathematical functions, or both. For example, the information for the melanin content can be used as an offset (e.g., additive offset), a scale factor, or both for adjusting the value for the oxygen saturation.

In an alternative implementation, at 494, the oximeter probe determines the absorption coefficient $\mu_a$ (mua), the reduced scattering coefficient $\mu_s'$ (mus), or both for the tissue for a number of wavelengths of light (e.g., four wavelengths of light) emitted and detected by the oximeter probe. Thereafter, the oximeter probe adjusts the determined absorption ($\mu_a$) values for each wavelength of light using the information about melanin content. The oximeter probe can adjust the absorption coefficient ($\mu_a$) values via one or more arithmetic operations, mathematical functions, or both. For example, the information for the melanin content can be used as an offset (e.g., additive offset), a scale factor, or both for adjusting the absorption ($\mu_a$) values. Thereafter, the oximeter probe uses the absorption ($\mu_a$) values to determine a value for the oxygen saturation for the tissue. Determination of absorption ($\mu_a$) and reduced scattering ($\mu_s'$) are described below.

In another implementation, at 494, the oximeter probe applies one or more melanin correction functions to reflectance data generated by the detector structures. The melanin correction functions are based on the information for the melanin content. The reflectance data can be analog reflectance data generated by the detector structures prior to being digitized by one or more electronic components of the oximeter probe or the reflectance data can be digitized reflectance data. The melanin correction functions can be applied to the analog reflectance data or the digitized reflectance data. The melanin correction function includes one or more mathematical operations that are applied to the reflectance data. The scale factors are determined by the oximeter probe based on information for the melanin content that is entered into the oximeter probe. The reflectance data can be adjusted for melanin content for each wavelength of light emitted by the oximeter probe.

In an implementation, the melanin correction function can be a combined function (e.g., having scale factors) that is combined with one or more calibration functions (e.g., having scale factors). The calibration function can include scale factors for correcting the detector responses based on a variety of factors, such as differences that occur as a result of manufacturing, that occur as a result of temperature drift of the detector structures, or other considerations. After the reflectance data are adjusted by the oximeter probe, the probe can then determine the oxygen saturation of blood in the tissue to be measured.

Figure 5:
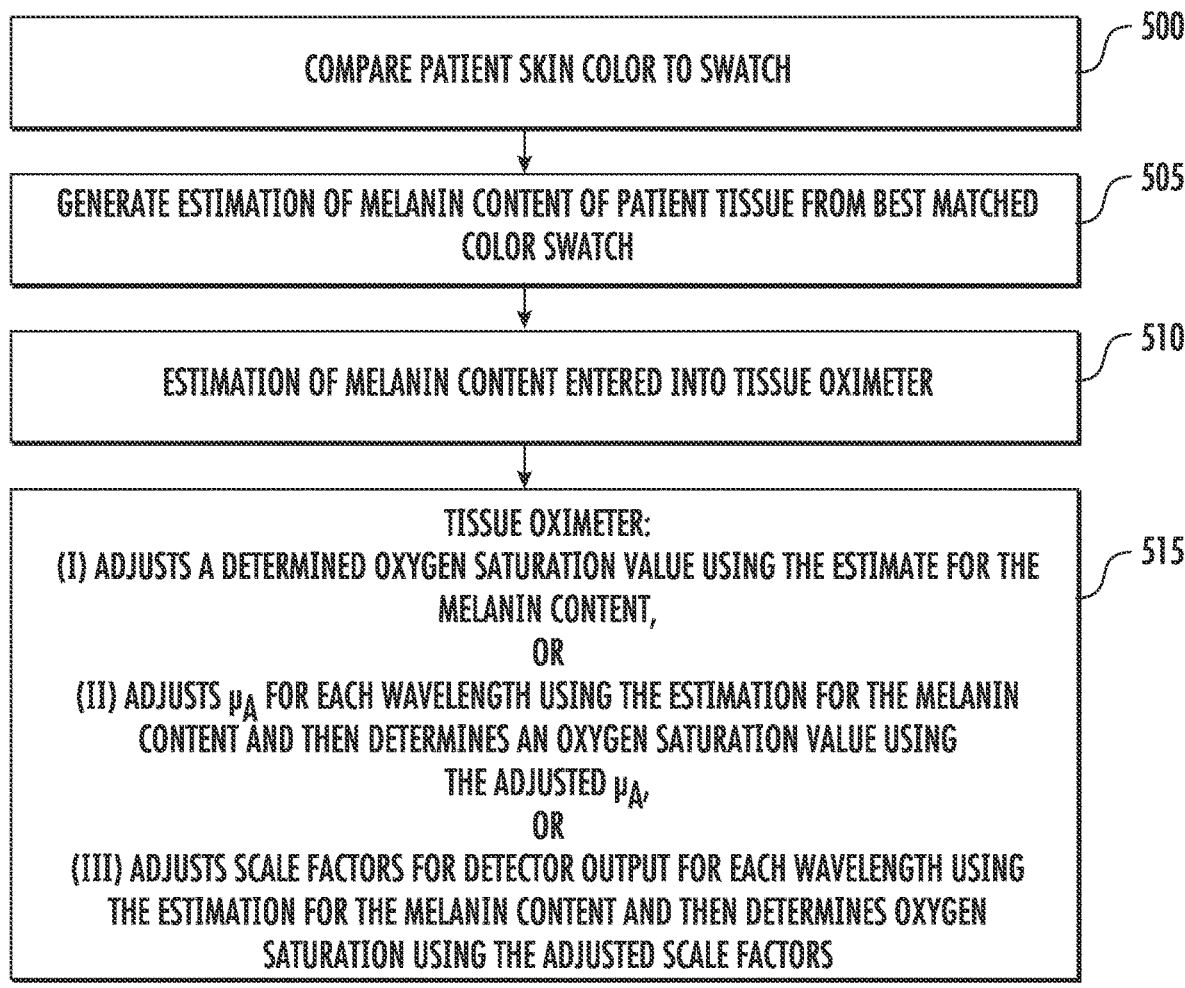
FIG. 5 shows a flow diagram of a method for determining optical properties of tissue by the oximeter probe in an implementation.

FIG. 5 shows a flow diagram of a method for determining optical properties of tissue by oximeter probe 101 in an implementation. The oximeter probe uses information about the melanin content for the tissue to correct various tissue parameters measured by the oximeter probe. The flow diagram represents one example implementation. Steps may be added to, removed from, or combined in the flow diagram without deviating from the scope of the implementation.

At 500, the color of the tissue is compared to two or more color samples of a number of color samples (sometimes referred to as color swatches) to determine whether the color of one of the color samples approximately matches the color of the tissue. Each color sample used for the color comparison is associated with a value of melanin content. Information (e.g., a numerical value) that identifies the melanin content for the color sample can be located on the color sample.

The comparison between the color of the tissue and the color of the color samples can be performed by a color comparison tool, such as one or more of the color comparison tools of X-Rite, Incorporated of Grand Rapids Michigan. In an implementation, the comparison can be performed visually by a human, such as the patient or a medical provider. In an implementation, the oximeter probe is adapted to determine a value for the melanin content of the tissue, which can displayed on the display of the probe.

At 505, subsequent to the comparison, the value for the melanin content of the tissue is determined based on the comparison.

In an alternative implementation, the value for the melanin content is determined from an estimate of the content based on a finite range of melanin content values. The number of values in a range for melanin content can include two or more values. For example, the number of values in a range for melanin contents can be 2 (e.g., 1 for light tissue and 2 for dark tissue), 3 (e.g., 1 for light, 2 for medium, and 3 dark), 4, 5, 6, 7, 8, 9, 10 or more. An estimation of the value for melanin content can be provided by the patient or a medical provider.

At 510, the information about the melanin content can be entered into the oximeter probe. Step 510 can be skipped in a method where the oximeter probe determines the value for the melanin content. Button 119 can be activated a predetermined number of times to place the oximeter probe into a data entry mode in which the information for the melanin content can be entered. The information for the melanin content can thereafter be entered into the probe by further activation of the button, via a wired communication with the probe, via a wireless communication with the probe, via the display if the display is a touch interface display, via an audible interface (e.g., a microphone and voice recognition software in the probe), or by other input techniques.

At 515, the oximeter probe is adapted to use information about the melanin content to adjust one or more measurements or calculations performed by the oximeter probe. For example, the oximeter probe can use the information to adjust oxygen saturation value for the tissue, adjust absorption ($\mu_a$), adjust reduced scattering ($\mu_s'$), adjust values generated by the detector(s), or one or more of a combination of these adjustments. Each of these adjustments is described further above with respect to step 435.

Figure 6:
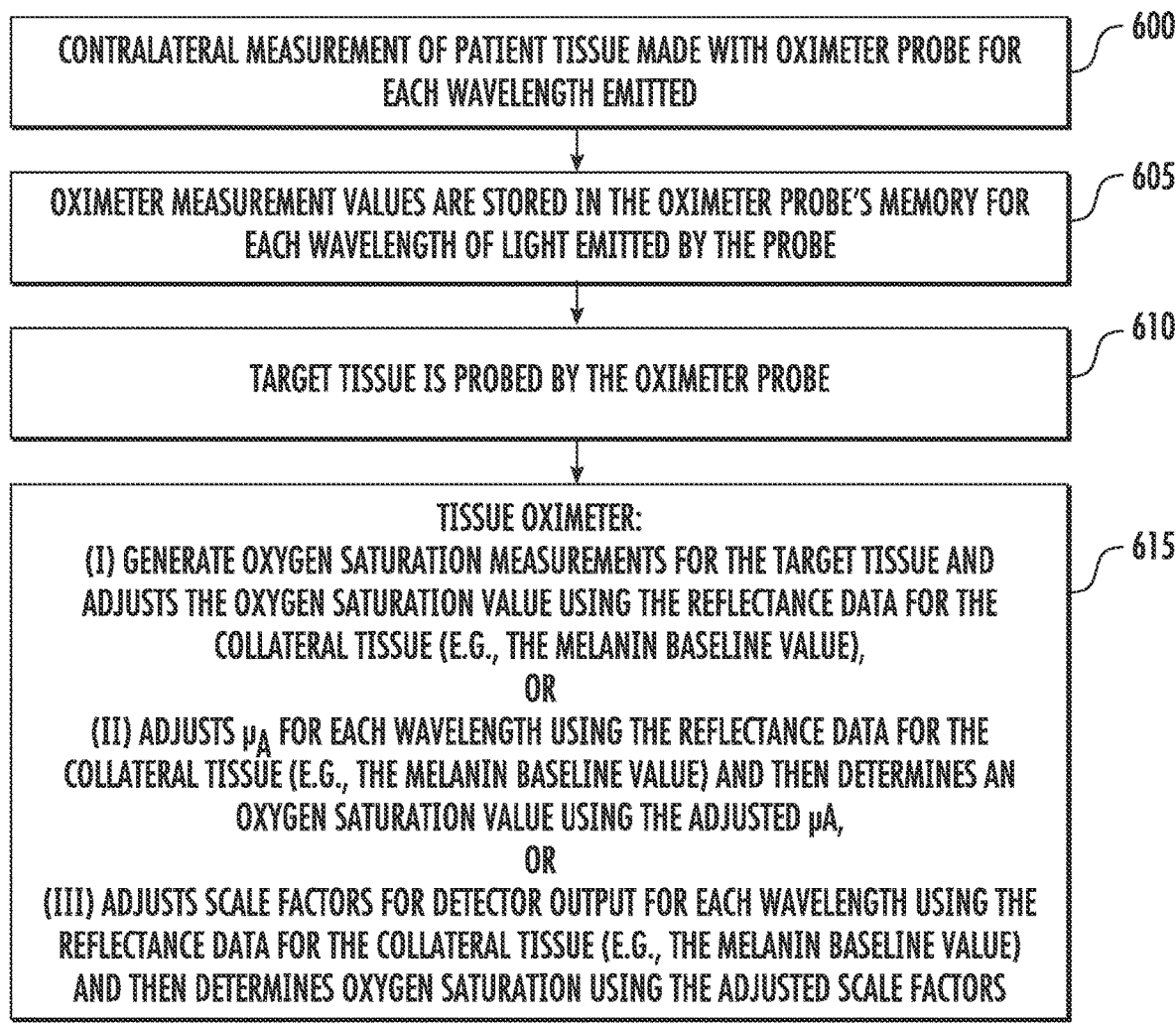
FIG. 6 shows a flow diagram of a method for determining optical properties of tissue by the oximeter probe in an implementation.

FIG. 6 shows a flow diagram of a method for determining optical properties of tissue by oximeter probe 101 in an implementation. The oximeter probe uses the determined melanin content of the tissue to correct various tissue parameters that are measured by the probe. The flow diagram represents one example implementation. Steps may be added to, removed from, or combined in the flow diagram without deviating from the scope of the implementation.

At 600, one or more contralateral measurements of the tissue are made with the oximeter probe. The contralateral measurements are made using the oximeter probe on a portion of healthy tissue (e.g., healthy breast tissue) before a measurement is made using the oximeter probe on target tissue that is to be measured (e.g., breast tissue for which tissue health is to be determined). The contralateral measurements of the tissue can be made for each wavelength of light emitted by the oximeter probe.

At 605, reflectance data generated by the detector structures are digitized by the electronic elements of the oximeter probe and are stored in memory. The reflectance data provide a basis of comparison for subsequent tissue measurement. For example, the contralateral measurements provide baseline measurements of the melanin content of the contralateral tissue where the baseline measurements can be used by the processor to correct for various measurements made the oximeter probe.

At 610, oximetry measurements of the target tissue to be measured are made by the oximeter probe.

At 615, in an implementation, the processor generates oxygen saturation values for target tissue using the oximetry measurements. Thereafter, the processor retrieves the stored reflectance data stored at 605 for the contralateral tissue and uses the retrieved values to adjust the oxygen saturation values. That is, the processor uses the baseline measurement for melanin content for the healthy contralateral tissues tissue to adjust the oxygen saturation values of the target tissue.

At 615, in an alternative implementation, the processor determines absorption $\mu_a$, reduced scattering coefficient or both from the oximetry measurements of the target tissue. Thereafter, the processor retrieves the reflectance data stored at 605 for the contralateral tissue and uses the retrieved values to adjust $\mu_a$, or both. The processor then uses the adjusted $\mu_a$ value to calculate values for oxygenated hemoglobin, deoxygenated hemoglobin, or other values for the target tissue. That is, the processor uses the baseline measurement for melanin content of the healthy contralateral tissue to adjust $\mu_a$ for the target tissue.

At 615, in an another alternative implementation, the processor retrieves the stored reflectance data stored at 605 for the contralateral tissue and uses the retrieved values to adjust the reflectance data generated by the detector structures for the target tissue. The adjustments applied by the processor to the reflectance data can be simple offsets (e.g., addition offsets), scale factors (e.g., multiplication offsets), functional corrections, other corrections, or any one or these adjustments in any combination. That is, the processor adjusts the values generated by the detector structures using the baseline measurement for melanin content for the healthy tissue to adjust the reflectance data for the target tissue.

Stored Simulated Reflectance Curves. According to an implementation, memory 117 stores a number of Monte-Carlo-simulated reflectance curves 315 ("simulated reflectance curves"), which may be generated by a computer for subsequent storage in the memory. Each of the simulated reflectance curves 315 represents a simulation of light (e.g., near infrared light) emitted from one or more simulated source structures into simulated tissue and reflected from the simulated tissue into one or more simulated detector structures. Simulated reflectance curves 315 are for a specific configuration of simulated source structures and simulated detector structures, such as the configuration of source structures 120a-120b and detector structures 125a-125h of probe tip 110 having the source-to-detector spacing described above with respect to FIG. 2.

Therefore, simulated reflectance curves 315 model light emitted from the source structures and collected by the detector structures of oximeter probe 101. Further, each of the simulated reflectance curves 315 represents a unique real tissue condition, such as specific tissue absorption and tissue scattering values that relate to particular concentrations of tissue chromophores and particular concentrations of tissue scatterers. For example, the simulated reflectance curves can be generated for simulated tissue having various melanin contents, various oxygenated hemoglobin concentrations, various deoxygenated hemoglobin concentrations, various concentrations of water, a static value for the concentrations of water, various concentration of fat, a static value for the concentration of fat, or various absorption ($\mu_a$) and reduced scattering ($\mu_s'$) values.

The number of simulated reflectance curves stored in memory 117 may be relatively large and can represent nearly all, if not all, practical combinations of optical properties and tissue properties that may be present in real tissue that is analyzed for viability by oximeter probe 101. While memory 117 is described as storing Monte-Carlo-simulated reflectance curves, memory 117 may store simulated reflectance curves generated by methods other than Monte-Carlo methods, such as using a diffusion approximation.

Figure 7:
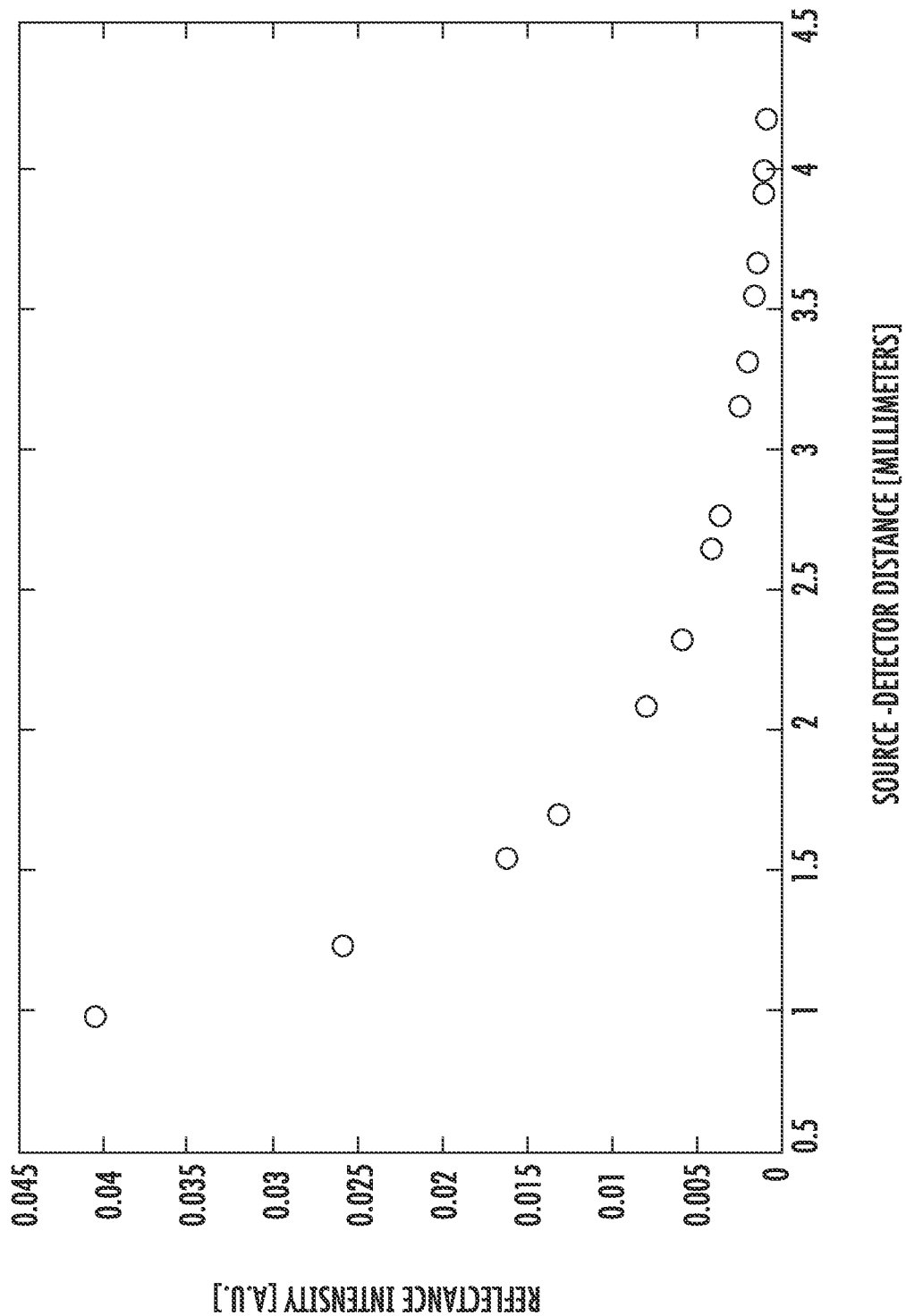
FIG. 7 shows an example graph of a reflectance curve, which may be for a specific configuration of source structures and detector structures, such as the configuration source structures and detector structures of the probe tip.

FIG. 7 shows an example graph of a reflectance curve, which may be for a specific configuration of source structures 120 and detector structures 125, such as the configuration source structures and detector structures of probe tip 110. The horizontal axis of the graph represents the distances between source structures 120 and detector structures 125 (i.e., source-to-detector distances). If the distances between source structures 120 and detector structures 125 are appropriately chosen, and the simulated reflectance curve is a simulation for source structures 120 and detector structures 125, then the lateral spacings between the data points in the simulated reflectance curve will be relatively uniform. Such uniform spacings can be seen in the simulated reflectance curve in FIG. 7. The vertical axis of the graph represents the simulated reflectance of light that reflects from tissue and is detected by detector structures 125. As shown by the simulated reflectance curve, the reflected light that reaches detector structures 125 varies with the distance between source structures and detectors structures, with the reflected light detected at smaller source-to-detectors distances greater than the reflected light detected a larger source-to-detector distances.

Figure 8:
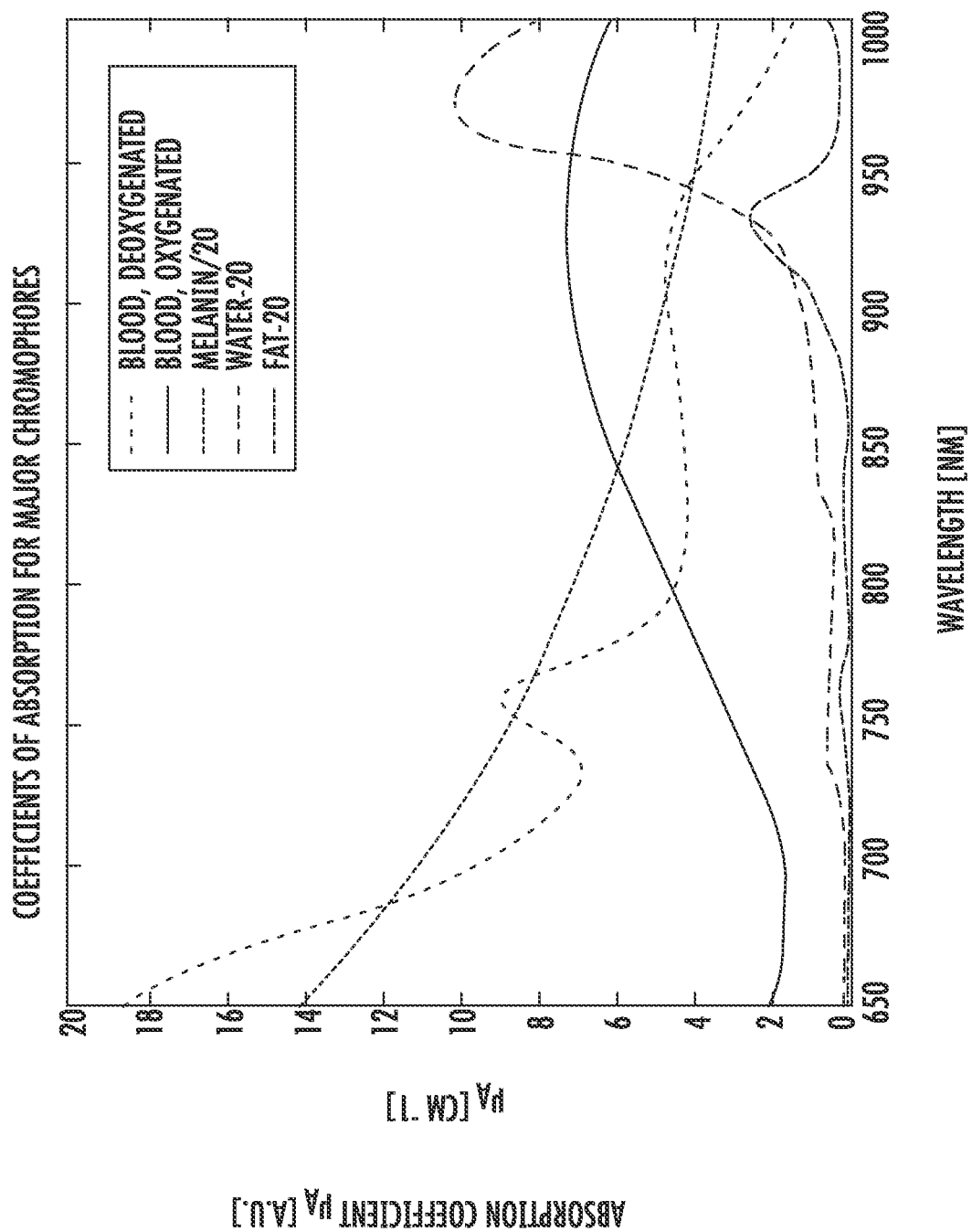
FIG. 8 shows a graph of the absorption coefficient $\mu a$ in arbitrary units versus wavelength of light for oxygenated hemoglobins, deoxygenated hemoglobins, melanin, and water in tissue.

FIG. 8 shows a graph of the absorption coefficient $\mu_a$ versus wavelength of light for some significant tissue chromophores: blood containing oxygenated hemoglobin, blood containing deoxygenated hemoglobin, melanin, and water. In an implementation, the Monte-Carlo simulations used for generating the simulated reflectance curve are functions of one or more select chromophores that may be present in tissue. The chromophores can include melanin, oxygenated hemoglobin, deoxygenated hemoglobin, water, lipid, cytochrome, or other chromophores, in any combination. Oxygenated hemoglobins, deoxygenated hemoglobins, and melanin are the most dominant chromophores in tissue for much of the visible and near-infrared spectral range.

In an implementation, memory 117 stores a select number of data points for each of the simulated reflectance curves 315 and might not store the entirety of the simulated reflectance curves. The number of data points stored for each of the simulated reflectance curves 315 may match the number of source-detector pairs. For example, if probe tip 110 includes two source structures 120a-120b and includes eight detector structures 125a-125h, then oximeter probe 101 includes sixteen source-detector pairs, and memory 117 may thus store sixteen select data points for each of the simulated reflectance curves for each wavelength of light emitted by source structure 120a or source structure 120b. In an implementation, the stored data points are for the specific source-to-detectors distances of probe tip 110, such as those shown in table 1.

Thus, the simulated reflectance curve database stored in memory 117 might be sized 16×5850 where sixteen points are stored per curve that may be generated and emitted by each source structure 120 and measured by each detector structure 125, where there are a total of 5850 curves spanning the optical property ranges. Alternatively, the simulated reflectance curve database stored in memory 117 might be sized 16×4×5850 where sixteen points are stored per curve for four different wavelengths that may be generated and emitted by each source structure and where there are a total of 5850 curves spanning the optical property ranges. The 5850 curves originate, for example, from a matrix of 39 scattering coefficients $\mu_s'$ values and 150 absorption coefficient $\mu_a$ values. In other implementations, more or fewer simulated reflectance curves are stored in the memory. For example, the number of simulated reflectance curves stored in memory can range from about 5000 curves, to about 250,000 curves, to about 400,000 curves, or more.

The reduced scattering coefficient $\mu_s'$ values might range from 5:5:24 per centimeter. The $\mu_a$ values might range from 0.01:0.01:1.5 per centimeter. It will be understood that the foregoing described ranges are example ranges and the number source-detectors pairs, the number of wavelengths generated and emitted by each source structure, and the number of simulated reflectance curves may be smaller or larger.

FIG. 9 shows a database 900 of simulated reflectance curves 315 that is stored in the memory of the oximeter probe in an implementation. The database is for a homogeneous model of tissue. Each row in the database represents one simulated reflectance curve generated from a Monte-Carlo simulation for simulated light emitted into simulated tissue from two simulated source structures (e.g., source structures 120a-120b) and detected by eight simulated detector structures (e.g., detector structures 125a-125h) subsequent to reflection from the simulated tissue. The Monte-Carlo simulations used for generating the simulated reflectance curves for the databases are for a homogeneous tissue model. The simulated tissue for the homogeneous tissue model has homogeneous optical properties from the tissue surface through the epidermis, the dermis, and the subcutaneous tissue. That is, the optical properties of the epidermis, dermis, and subcutataneous are the same for the Monte-Carlo simulations. In the database, each of the simulated reflectance curves is associated with a value for absorption ($\mu_a$) and a value for reduced scattering ($\mu_s'$). Each of the simulated reflectance curves in the database can be associated with values for other chromophores.

The database of simulated reflectance curves can include actual values (e.g., floating point values) for simulated reflectances or can include indexed values (e.g., binary values) for the actual values for the simulated reflectances. As shown in FIG. 9, the database includes indexed values (e.g., binary values) for the actual values for the simulated reflectances. The database can include binary words of a variety of lengths dependent, for example, on the accuracy of the entries. The binary words can be 2 bits long, 4 bits long, 8 bits long, 16 bits long, 32 bits long, or other lengths.

In an implementation, one or more mathematical transforms are applied to the simulated reflectance curves prior to entry of the values for the curves into the database. The mathematical transforms can improve the fit of the reflectance data generated by the detector structures to the simulated reflectance curves. For example, a log function can be applied to the simulated reflectance curves to improve the fit of the measured data generated by the detector structures to the simulated reflectance curves.

When an oximetry measurement is made, the reflectance data for each wavelength of emitted light is detected by the detector structures and fitted to the simulated reflectance curves of database 900 individually. For the reflectance data for each wavelength of emitted light fitted to the simulated reflectance curves, the oximeter probe determines absorption $\mu_a$, reduced scattering $\mu_s'$ or both of these values. For example, a first set of reflectance data for a first wavelength of light is fitted to the simulated reflectance curves to determine one or more of absorption $\mu_a$, and reduced scattering $\mu_s'$ (e.g., a first set of tissue parameters). Fitting the reflectance data to the simulated reflectance curves is described further below.

Thereafter, a second set of reflectance data for a second wavelength of light is fitted to the simulated reflectance curves in database 900 to determine one or more of absorption $\mu_a$, and reduced scattering $\mu_s'$ (e.g., a second set of tissue parameters) for the second wavelength. Thereafter, a third set of reflectance data for a third wavelength of light is fitted to the simulated reflectance curves in database 900 to determine one or more of absorption $\mu_a$, and reduced scattering $\mu_s'$ (e.g., a third set of tissue parameters). Thereafter, a fourth set of reflectance data for a fourth wavelength of light is fitted to the simulated reflectance curves in database 900 to determine one or more of absorption $\mu_a$, and reduced scattering $\mu_s'$ (e.g., a fourth set of tissue parameters) for the fourth wavelength.

The four sets of tissue parameters can then be used by the oximeter probe together to determine various values for the tissue, such as oxygenated hemoglobin concentration, deoxygenated hemoglobin concentration, melanin content, or other parameters.

Figure 10:
FIG. 10 shows a table for a database for a layered model of tissue of simulated reflectance curves that is stored in the memory of the oximeter probe in an implementation.

FIG. 10 shows a database 1000 of simulated reflectance curves that is stored in the memory of the oximeter probe in an implementation. The database is for a layered model of tissue (e.g. layered skin). The Monte-Carlo simulations that generated the simulated reflectance curves use the layered tissue model for the simulations. The layered tissue can include two or more layers. In an implementation, the layered tissue includes two layers of tissue. The two layers of tissue have different optical properties, such as different absorption $\mu_a$, reduced scattering $\mu_s'$, or both of these properties.

In one implementation, a first simulated tissue layer is for the epidermis and a second simulated tissue layer is for the dermis. The thickness of the epidermis used in the Monte-Carlo simulations can range from about 40 microns to about 140 microns. For example, the thickness for the epidermis can be 40 microns, 50 microns, 60 microns, 70 microns, 80 microns, 90 microns, 100 microns, 110 microns, 120 microns, 130 microns, 140 microns, or other thickness. The thickness of the dermis used in the Monte-Carlo simulations can range from less than 1 millimeter to an effectively infinite thickness, such as 12 millimeters or greater.

One or more optical properties of the epidermis can be varied when the simulated reflectance curves are generated for the dermis. For example, melanin content can be varied for the epidermis when the simulation reflectance curves are generated for the dermis. Alternatively, $\mu_a$ can be varied for the epidermis when the simulation reflectance curves are generated for the dermis.

In an implementation, database 1000 includes the simulated reflectance curves for the light that is reflected by the combination of the epidermis and the dermis.

The reflectance data for each wavelength of light emitted by the source structures and detected by the detector structures for real tissue measured by the oximeter probe is fit to the simulated reflectance curves one at a time by the processor. Based on the fit to one or more the simulated reflectance curves in the database, the oximeter probe determines one or both of the absorption $\mu_a$ and reduced scattering $\mu_s'$ for the real tissue for one or both layers. From the absorption ($\mu_a$) values determined for one layer, the oximeter probe determines the oxygenated and deoxygenated hemoglobin concentrations for the tissue.

Figure 11A:
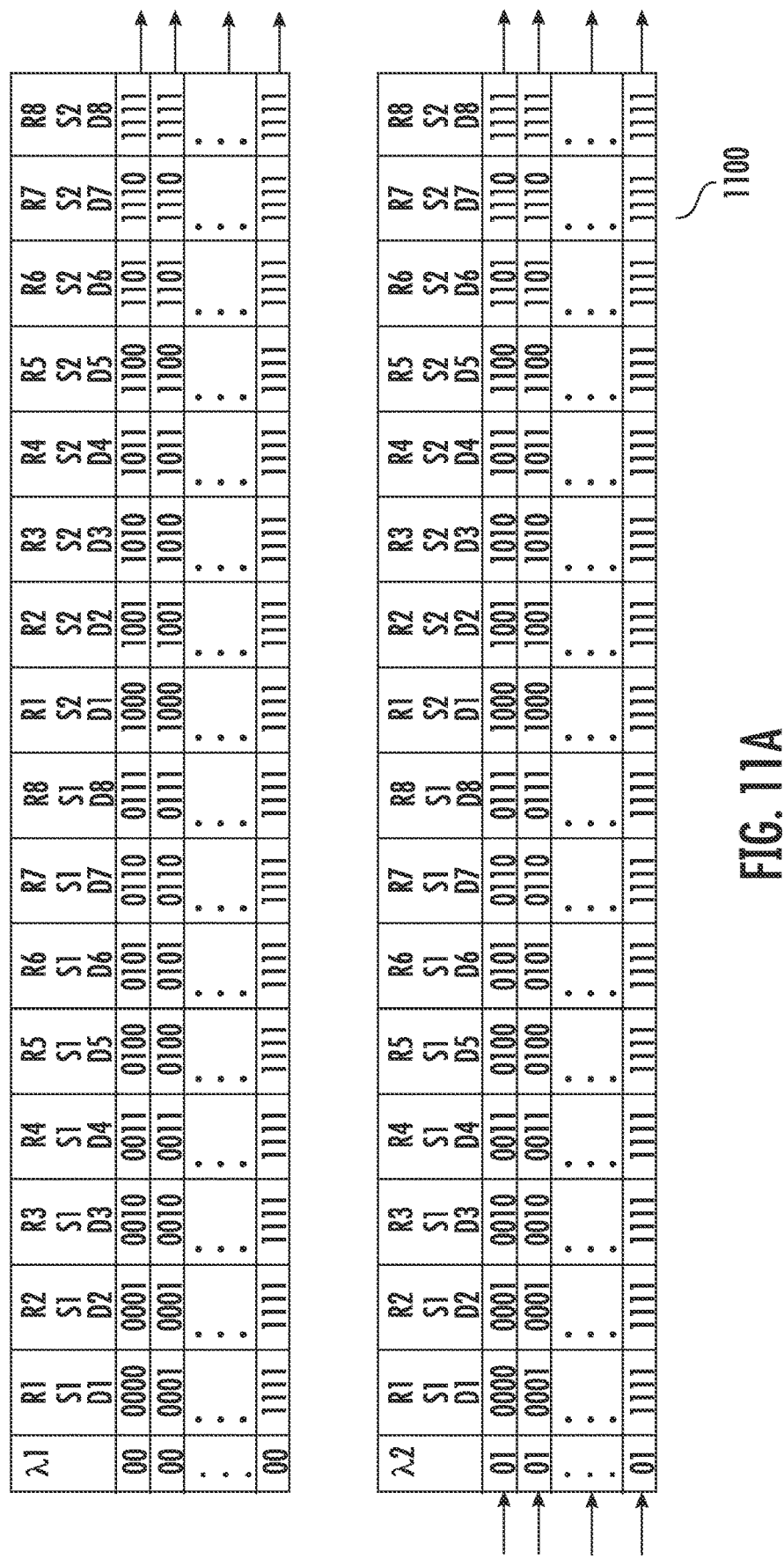
Figure 11B:
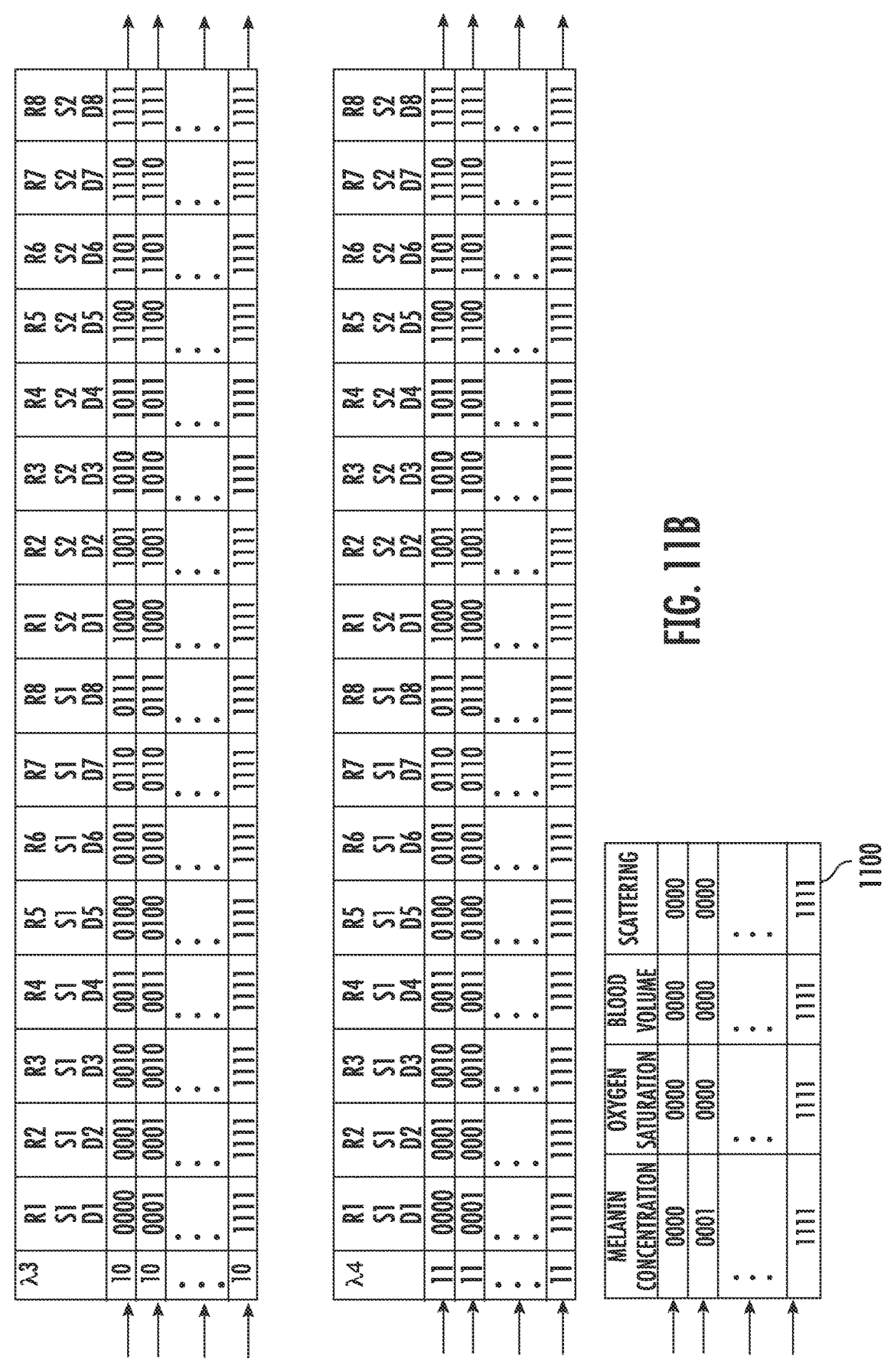

FIGS. 11A-11B show a database 1110 of simulated reflectance curves stored in the memory of the oximeter probe in an implementation. The database is for a layered model of tissue. Each row in the database includes simulated reflectance curves for each of four wavelengths of light emitted from the simulated source structures and detected by simulated detector structures. Each row of four simulated reflectance curves includes 16 values for each simulated reflectance curve. More specifically, each row includes 16 values for the 16 source-to-detector distances for source structures 120*a*-120*b* and detector structures 125*a*-125*h*. In total, each row includes 64 values for the four simulated reflectance curves for four wavelengths of light emitted from the two simulated source structures and detected by the eight simulated detector structures.

The layered model of tissue for database 1110 can include more or fewer simulated reflectance curves per row if more or fewer wavelengths are emitted from the source structures. Database 1110 can include more or fewer then 16 values for each of simulated reflectance curves if, for example, one or more than two source structure is included in the probe tip, more or fewer detector structures are included in the probe tip, or both.

Each of the four simulated reflectance curves for each row of database 1110 is associated with four tissue parameters, including melanin content, blood volume, scattering, and oxygen saturation (the fraction of oxygenated hemoglobin relative to total hemoglobin for tissue). More of fewer tissue parameters can be included in database 1110.

When a set of detector values that are generated by detector structures 125*a*-125*h* for tissue to be measured by the oximeter probe are fit by the processor to one or more of the rows, the oximeter probe thereby determines, in any combination, one or more of the tissue parameters such as melanin content, blood volume, scattering, and oxygen saturation. In an implementation, the oximeter probe is adapted to determine the oxygen saturation for the tissue and display a value for the oxygen saturation on the display.

As described briefly above, database 1110 includes simulated reflectance curves 315 for a layered tissue model. The layers of the simulated tissue can include the epidermis, the dermis, subcutaneous tissue, or any combination of one or more of these layers. The layers can include greater resolution of skin morphology such as the reticular dermis and superficial plexus. The Monte-Carlo simulations that generate the simulated reflectance curve can simulate the tissue for various chromophores included in the tissue layers. For example, the Monte-Carlo simulations can use a tissue model for the epidermis having various melanin contents, but might not use a tissue model for epidermis that includes blood. The Monte-Carlo simulations can use a tissue model for the dermis layer having various blood volumes and various oxygen saturations. In an implementation, the Monte-Carlo simulations do not use a tissue model for dermis that includes melanin. Similarly, the Monte-Carlo simulations can use a tissue model of adipose tissue having various blood volumes and various oxygen saturations. In an implementation, the Monte-Carlo simulations do not use a tissue model for adipose tissue that has melanin. The tissue models for the tissue layers can include concentrations for other tissue chromophores, such as water and fat where the concentrations for these chromophores are relatively typical physiological values.

In an implementation, the various chromophore concentrations that the Monte-Carlo simulations use for generating the simulated reflectance curves span a relatively large and relatively accurate range of actual physiological values present in real tissue. The number of values included in the ranges of actual physiological values can be varied to balance various parameters of tissue oximeter measurements. For example, the number of values used for the range of concentrations of the chromophores in simulated tissue can be relatively high or low and affect the accuracy of measurements made by the oximeter probe. In an implementation, 355 values are used in the Monte-Carlo simulations for the range of melanin content for light absorption in simulated epidermal tissue. In an implementation, 86 values are used in the Monte-Carlo simulations for the range of melanin content for light absorption in simulated dermal tissue. For scattering in both simulated epidermal tissue and simulated dermal tissue, 65 values are used in the Monte-Carlo simulations. In other implementations, the number of these values is different.

Figure 12A:
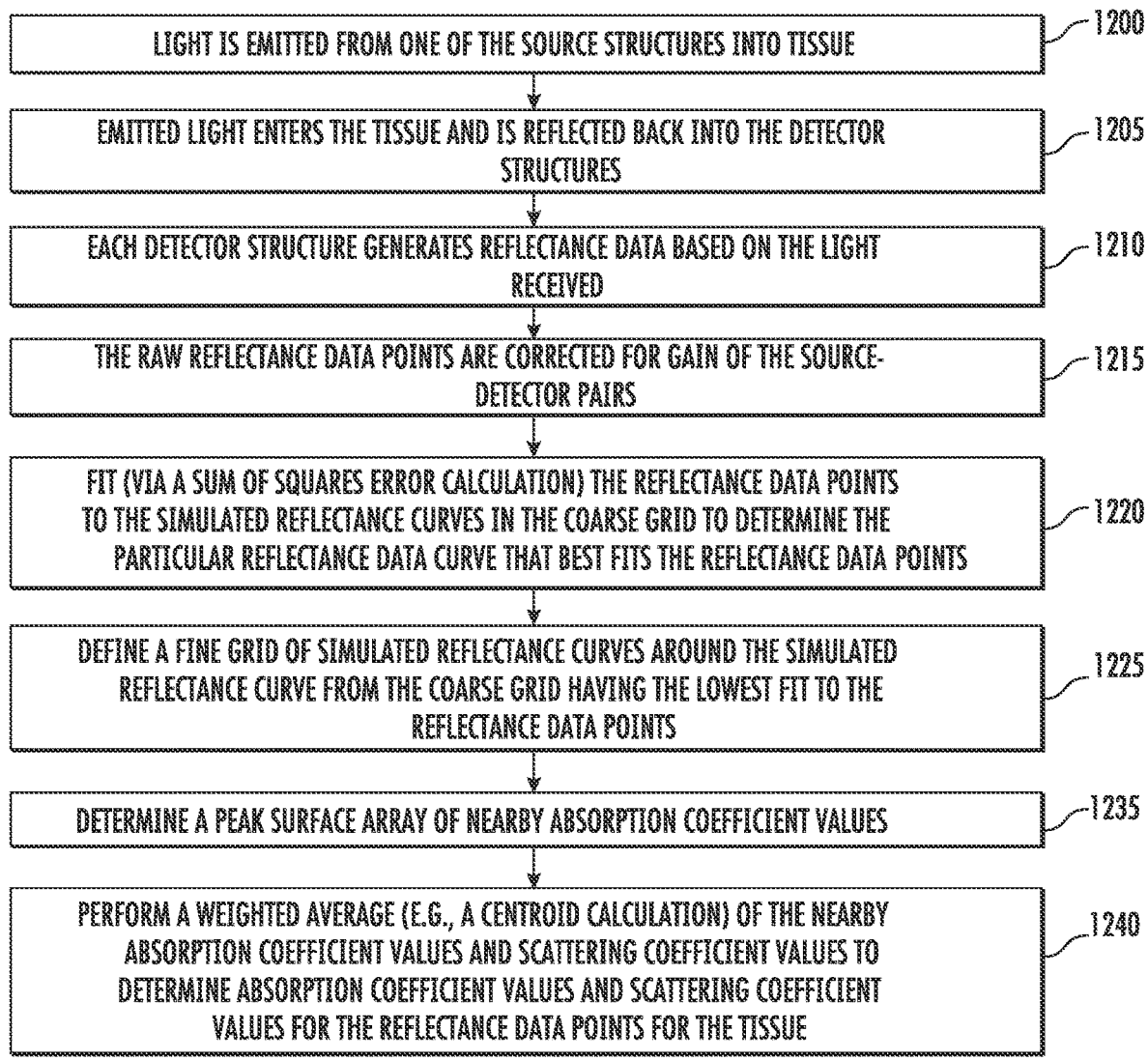
FIGS. 12A-12B show a flow diagram of a method for determining the optical properties of tissue (e.g., real tissue) by the oximeter probe where the oximeter probe uses reflectance data and the simulated reflectance curves to determine the optical properties.
Figure 12B:
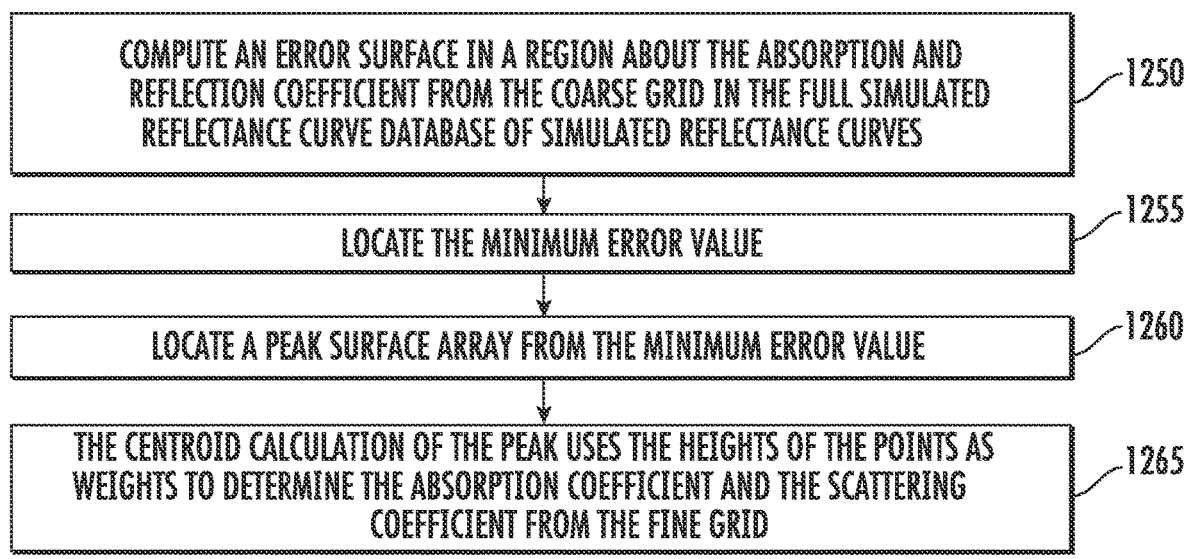

Tissue Analysis. FIGS. 12A and 12B show a flow diagram of a method for determining the optical properties of tissue (e.g., skin) by oximeter probe 101 where the oximeter probe uses reflectance data and simulated reflectance curves 315 to determine the optical properties. The optical properties may include the absorption coefficient $\mu_a$ and the reduced scattering coefficient of the tissue. A further method for conversion of the absorption coefficient $\mu_a$ of the tissue to oxygen saturation values for tissue is described in further detail below. The flow diagram represents one example implementation. Steps may be added to, removed from, or combined in the flow diagram without deviating from the scope of the implementation.

At 1200, oximeter probe 101 emits light (e.g., near infrared light) from one of the source structures 120, such as source structure 120*a* into tissue. The oximeter probe is generally in contact with the tissue when the light is emitted from the source structure. After the emitted light reflects from the tissue, detector structures 125 detect a portion this light, step 1205, and generate reflectance data points for the tissue, step 1210. Steps 1200, 1205, and 1210 may be repeated for multiple wavelengths of light (e.g., red, near infrared light, or both) and for one or more other source structures, such as source structure 120*b*. The reflectance data points for a single wavelength might include sixteen reflectance data points if, for example, tissue oximeter probe 115 has sixteen source-to-detector distances. The reflectance data points are sometimes referred to as an N-vector of the reflectance data points.

At 1215, the reflectance data points (e.g., raw reflectance data points) are corrected for gain of the source-detector pairs. During calibration of the source-detector pairs, gain corrections are generated for the source-detector pairs and are stored in memory 117. Generation of the gain corrections is described in further detail below.

At 1220, processor 116 fits (e.g., via a sum of squares error calculation) the reflectance data points to the simulated reflectance curves 315 to determine the particular reflectance data curve that best fits (i.e., has the lowest fit error) the reflectance data points. The database stored in the memory and fit to the reflectance data can be database 900, database 1000, or database 1100. In a specific implementation, a relatively small set of simulated reflectance curves that are a "coarse" grid of the database of the simulated reflectance curves is selected and utilized for fitting step 1220. For example, for database 900 given 39 scattering coefficient $\mu_s'$ values and 150 absorption coefficient $\mu_a$ values, a coarse grid of simulated reflectance curves might be determined by processor 116 by taking every 5th scattering coefficient $\mu_s'$ value and every 8th absorption coefficients $\mu_a$ for a total of 40 simulated reflectance curves in the coarse grid. It will be understood that the foregoing specific values are for an example implementation and that coarse grids of other sizes might be utilized by processor 116. The result of fitting the reflectance data points to the coarse grid is a coordinate in the coarse grid $(\mu_s, \mu_s')_{coarse}$ of the best fitting simulated reflectance curve. For database 1000, the coarse grid will cover absorption in each layer and reduced scattering. Each of the following steps for the method for database 1000 will be adjusted for $\mu_a$ of each layer and $\mu_s'$. For database 1100, the coarse grid will cover melanin content, oxygen saturation, blood volume, and scattering. Each of the following steps for the method for database 1100 will be adjusted for melanin content, oxygen saturation, blood volume, and scattering instead of $\mu_a$ and $\mu_s'$.

At 1225, the particular simulated reflectance curve from the coarse grid having the lowest fit error is utilized by processor 116 to define a "fine" grid of simulated reflectance curves where the simulated reflectance curves in the fine grid are around the simulated reflectance curve from the coarse grid having the lowest fit error.

That is, the fine grid is a defined size, with the lowest error simulated reflectance curve from the coarse grid defining the center of the fine grid. The fine grid may have the same number of simulated reflectance curves as the coarse grid or it may have more or fewer simulated reflectance curves. The fine grid is fine so as to provide a sufficient number of points to determine a peak surface array of nearby absorption coefficient $\mu_a$ values and scattering coefficient $\mu_s'$ values, step 1230, in the fine grid. Specifically, a threshold may be set by processor 116 utilizing the lowest error value from the coarse grid plus a specified offset. The positions of the scattering coefficient $\mu_s'$ and the absorption coefficient $\mu_a$ on the fine grid that have errors below the threshold may all be identified for use in determining the peak surface array for further determining the scattering coefficient $\mu_s'$ and the absorption coefficient $\mu_a$ for the reflectance data. Specifically, an error fit is made for the peak to determine the absorption coefficient $\mu_a$ and the scattering coefficient $\mu_s'$ values at the peak. A weighted average (e.g., a centroid calculation) of the absorption coefficient $\mu_a$ and the scattering coefficient $\mu_s'$ values at the peak may be utilized by the oximeter probe for the determination of the absorption coefficient $\mu_a$ and the scattering coefficient $\mu_s'$ values for the reflectance data points for the tissue, step 1240.

Weights for the absorption coefficient $\mu_a$ and the scattering coefficient $\mu_s'$ values for the weighted average may be determined by processor 116 as the threshold minus the fine grid error. Because points on the fine grid are selected with errors below the threshold, this gives positive weights. The weighted calculation of the weighted average (e.g., centroid calculation) renders the predicted scattering coefficient $\mu_s'$ and absorption coefficient $\mu_a$ (i.e., $(\mu_a, \mu_s')_{fine}$) for the reflectance data points for the tissue. Other methods may be utilized by the oximeter probe, such as fitting with one or more of a variety of non-linear least squares to determine the true minimum error peak for the absorption coefficient $\mu_a$.

In an implementation, processor 116 calculates the log of the reflectance data points and the simulated reflectance curves, and divides each log by the square root of the source-to-detector distances (e.g., in centimeters). These log values divided by the square root of the of the source-to-detector distances may be utilized by processor 116 for the reflectance data points and the simulated reflectance curves in the foregoing described steps (e.g., steps 1215, 1220, 1225, and 1230) to improve the fit of the reflectance data points to the simulated reflectance curves.

According to another implementation, the offset is set essentially to zero, which effectively gives an offset of the difference between the coarse grid minimum and the fine grid minimum. The method described above with respect to FIG. 12A relies on minimum fit error from the coarse grid, so the true minimum error on the fine grid is typically lower. Ideally, the threshold is determined from the lowest error on the fine grid, which would typically require additional computation by the processor.

The following is a further detailed description for finding the particular simulated reflectance curve that best fits the reflectance data points in the fine grid in an implementation. FIG. 12B shows a flow diagram of a method for finding the particular simulated reflectance curve that best fits the reflectance data points in the fine grid in an implementation. The flow diagram represents one example implementation. Steps may be added to, removed from, or combined in the flow diagram without deviating from the scope of the implementation.

Subsequent to determining the particular simulated reflectance curve $(\mu_a, \mu_s')_{coarse}$ from the coarse grid that best fits the reflectance data points at step 1225, processor 116 computes an error surface in a region about $(\mu_a, \mu_s')_{coarse}$ in the full simulated reflectance curve database (i.e., 16×5850 $(\mu_a, \mu_s')$database) of simulated reflectance curves, step 1250. The error surface is denoted as: $err(\mu_a, \mu_s')$. Thereafter, processor 116 locates the minimum error value in $err(\mu_a, \mu_s')$, which is referred to as $err_{min}$, step 1255. Processor 116 then generates a peak surface array from $err(\mu_a, \mu_s')$ that is denoted by $pksurf(\mu_a, \mu_s')=k+err_{min}-err(\mu_a, \mu_s')$ if the peak surface is greater than zero, or $pksurf(\mu_a, \mu_s')=k+err_{min}-err(\mu_a, \mu_s')=0$ if the peak surface is less than or equal to zero, step 1260. In the expression k is chosen from a peak at the minimum point of $err(\mu_a, \mu_s)$ with a width above zero of approximately ten elements. The center-of-mass (i.e., the centroid calculation) of the peak in $pksurf(\mu_a, \mu_s')$ uses the heights of the points as weights, step 1265. The position of the center-of-mass is the interpolated result for the absorption coefficient $\mu_a$ and the scattering coefficient $\mu_s'$ for the reflectance data points for the tissue The method described above with respect to FIGS. 12A and 12B for determining the absorption coefficient $\mu_a$ and the scattering coefficient $\mu_s'$ for reflectance data points for tissue may be repeated for each of the wavelengths (e.g., 3 or 4 wavelengths) generated by each of source structures 120.

Oxygen Saturation Determination. According to a first implementation, processor 116 determines the oxygen saturation for tissue that is probed by oximeter probe 101 by utilizing the absorption coefficients $\mu_a$ (e.g., 3 or 4 absorption coefficients $\mu_a$) that are determined (as described above) for the 3 or 4 wavelengths of light that are generated by each source structure 120. According to a first implementation, a look-up table of oxygen saturation values is generated for finding the best fit of the absorption coefficients $\mu_a$ to the oxygen saturation. The look-up table may be generated by assuming a range of likely total hemoglobin, melanin, and oxygen saturation values and calculating $\mu_a$ for each of these scenarios. Then, the absorption coefficient $\mu_a$ points are converted to a unit vector by dividing by a norm of the unit vector to reduce systematic error and only depend on relative shape of curve. Then the unit vector is compared to the look-up table to find the best fit, which gives the oxygen saturation.

According to a second implementation, processor 116 determines the oxygen saturation for the tissue by calculating the net analyte signal (NAS) of deoxygenated hemoglobin and oxygenated hemoglobin. The NAS is defined as the portion of the spectrum that is orthogonal to the other spectral components in the system. For example, the NAS of a deoxygenated hemoglobin in a system that also contains oxygenated hemoglobin and deoxygenated hemoglobin is the portion of the spectrum that is orthogonal to the oxygenated hemoglobin spectrum and the melanin spectrum. The concentrations of deoxygenated and oxygenated hemoglobin can be calculated by vector multiplying the respective NAS by the previously determined absorption coefficients at each wavelength. Oxygen saturation is then readily calculated as the concentration of oxygenated hemoglobin divided by the sum of oxygenated hemoglobin and deoxygenated hemoglobin. Anal. Chem. 58:1167-1172 (1986) by Lorber is incorporated by reference herein and provides a framework for a further detailed understanding of the second implementation for determining the oxygen saturation for the tissue.

In an implementation of oximeter probe 101, the reflectance data is generated by detector structures 125 at 30 Hertz, and oxygen saturation values are calculated at approximately 3 Hertz. A running average of determined oxygen saturation values (e.g., at least three oxygen saturation values) may be displayed on display 115, which might have an update rate of 1 Hertz.

Optical Properties. As described briefly above, each simulated reflectance curve 315 that is stored in memory 117 represents unique optical properties of tissue. More specifically, the unique shapes of the simulated reflectance curves, for a given wavelength, represent unique values of the optical properties of tissue, namely the scattering coefficient ($\mu_s$), the absorption coefficient ($\mu_a$), the anisotropy of the tissue (g), and index of refraction of the tissue from which the tissue properties may be determined.

The reflectance detected by detector structures 125 for relatively small source-to-detector distances is primarily dependent on the reduced scattering coefficient, $\mu_s'$. The reduced scattering coefficient is a "lumped" property that incorporates the scattering coefficient $\mu_s$ and the anisotropy g of the tissue where $\mu_s'=\mu_s(1-g)$, and is used to describe the diffusion of photons in a random walk of many steps of size of $1/\mu_s'$ where each step involves isotropic scattering. Such a description is equivalent to a description of photon movement using many small steps $1/\mu_s$ which each involve only a partial deflection angle if there are many scattering events before an absorption event, i.e., $\mu_a \ll \mu_s'$.

In contrast, the reflectance that is detected by detector structures 125 for relatively large source-to-detector distances is primarily dependent on the effective absorption coefficient $\mu_{eff}$, which is defined as $\sqrt{3\mu_a(\mu_a+\mu_s')}$, which is a function of both $\mu_a$ and $\mu_s'$.

Thus, by measuring reflectance at relatively small source-to-detector distances (e.g., S1-D4 and S2-D8 of FIG. 2) and relatively large source-to-detector distances (e.g., S1-D8 and S2-D4 of FIG. 2), both $\mu_a$ and $\mu_s'$ can be independently determined from one another. The optical properties of the tissue can in turn provide sufficient information for the calculation of oxygenated hemoglobin and deoxygenated hemoglobin concentrations and hence the oxygen saturation of the tissue.

Figure 13:
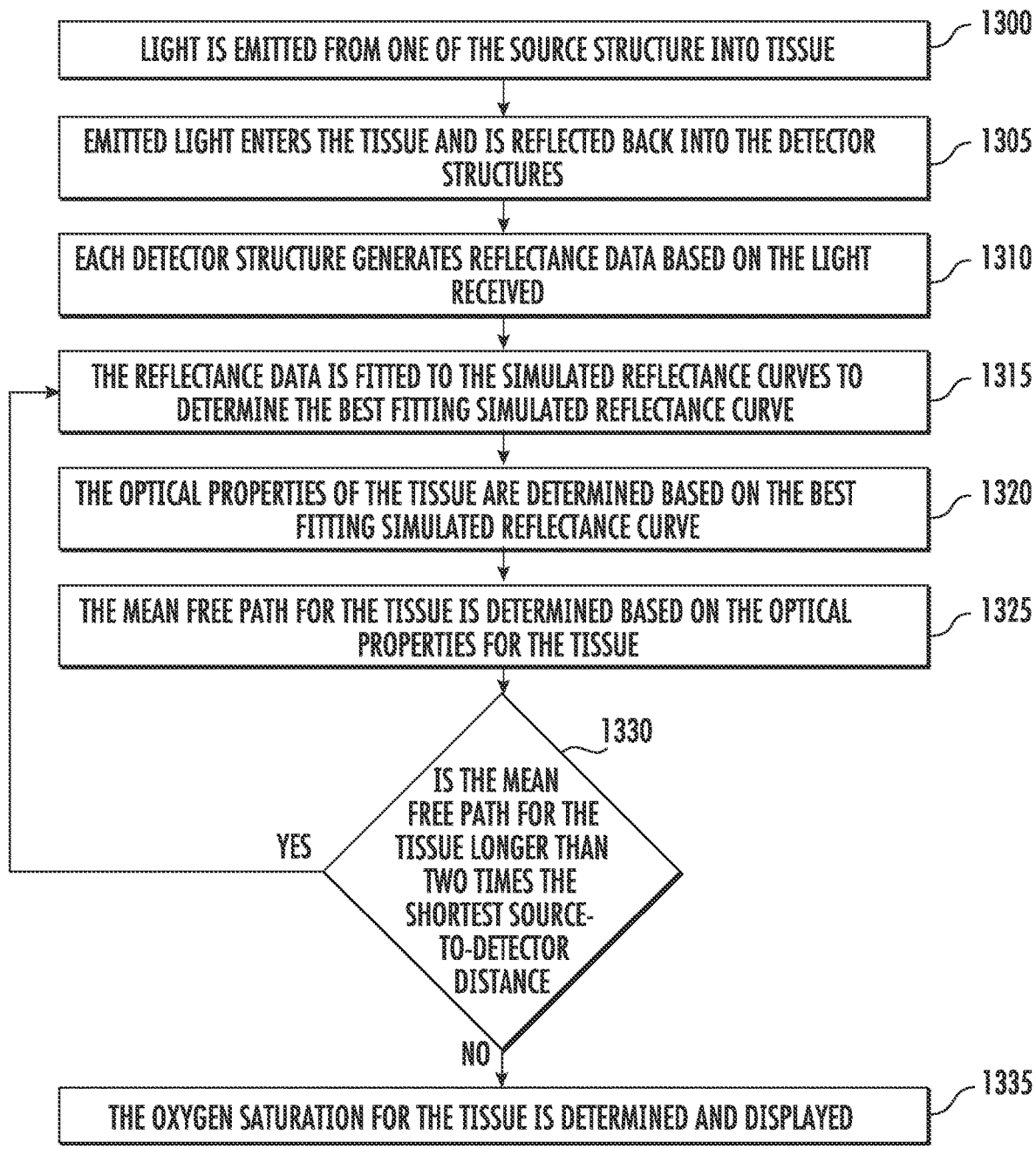
FIG. 13 shows a flow diagram of another method for determining the optical properties of tissue by the oximeter probe.

Iterative Fit for Data Collection Optimization. FIG. 13 shows a flow diagram of another method for determining the optical properties of tissue by oximeter probe 101. The flow diagram represents one example implementation. Steps may be added to, removed from, or combined in the flow diagram without deviating from the scope of the implementation.

At 1300, oximeter probe 101 emits light (e.g., near infrared light) from one of the source structures, such as source structure 120*a* into tissue. After the emitted light reflects from the tissue, detector structures 125 detect the light, step 1305, and generate reflectance data for the tissue, step 1310. Steps 1300, 1305, and 1310 may be repeated for multiple wavelengths of light and for one or more other source structures, such as source structure 120*b*. At 1315, oximeter probe 101 fits the reflectance data to simulated reflectance curves 315 and determines the simulated reflectance curve to which the reflectance data has the best fit. The database stored in the memory and fit to the reflectance data can be database 900, database 1000, or database 1100. Thereafter, oximeter probe 101 determines the optical properties (e.g., $\mu_a$, and $\mu_s'$ for database 900 or database 1000, or melanin content, oxygen saturation, blood volume, and scattering for database 1100) for the tissue based on the optical properties of the simulated reflectance curve that best fits the reflectance data, step 1320.

At 1325 oximeter probe 101 determines the mean free path of the light in the tissue from the optical properties (e.g., mfp=$1/(\mu_a+\mu_s')$) determined at step 1320. Specifically, the mean free path can be determined from the optical properties obtained from a cumulative reflectance curve that includes the reflectance data for all of the source-detector pairs (e.g., pair 1: source structure 120*a* and detector structure 125*a*; pair 2: source structure 120*a* and detector structure 125*b*; pair 3: source structure 120*a* and detector structure 125*c*; pair 4: source structure 120*a* and detector structure 125*d*; pair 5: source structure 120*a* and detector structure 125*e*; pair 6: source structure 120*a* and detector structure 125*f*; pair 7: source structure 120*a* and detector structure 125*g*; pair 8: source structure 120*a* and detector structure 125*h*; pair 9: source structure 120*b* and detector structure 125*a*, pair 10: source structure 120*b* and detector structure 125*b* . . . and others).

At 1330, oximeter probe 101 determines whether the mean free path calculated for a given region of the tissue is longer than two times the shortest source-to-detector distance (e.g., S1-D4 and S2-D8 of FIG. 2). If the mean free path is longer than two times the shortest source-to-detector distance, then the collected reflectance data is re-fitted to the simulated reflectance curves (i.e., reanalyzed) without utilizing the reflectance data collected from the detector structures for the source-to-detector pairs having the shortest source-to-detector distance. For example, steps 1315-1330 are repeated without use of the reflectance data from detector structure 125*e* with source structure 120*a* acting as the source for detector structure 125*d*, and without use of the reflectance data from detector structure 125*h* with source structure 120*b* acting as the source for detector structure 125*h*. The process of calculating the mean free path and discarding the reflectance data for one or more source-detector pairs may be repeated until no source-detector pairs that contribute reflectance data to the fit have a source-to-detector distance shorter than one half of the calculated mean free path. Thereafter, oxygen saturation is determined from the best fitting simulated reflectance curve and reported by oximeter probe 101, such as on display 115, step 1335.

Light that is emitted from one of the source structures 120 into tissue and that travels less than half of the mean free path is nondiffusely reflected or approximately nondiffusely reflected (e.g., there is a component of reflected light that is diffuse). The re-emission distance for this light is strongly dependent on the tissue phase function and the local tissue composition. Therefore, using the reflectance data for this light tends to result in a less accurate determination of the optical properties and tissue properties as compared with the reflectance data for light that has undergone multiple scattering events.

Data Weighting Detector Structures. Detector structures 125 that are positioned at increasing distances from source structures 120 receive decreasing amounts of reflectance from tissue. Therefore, the reflectance data generated by detector structures 125 having relatively short source-to-detector distances (e.g., S1-D4 and S2-D8 of FIG. 2) tends to exhibit intrinsically higher signal compared to reflectance data generated by detector structures having relatively long source-to-detector distances (e.g., S1-D8 and S2-D4 of FIG. 2). Fit algorithms may therefore preferentially fit the simulated reflectance curves to the reflectance data that is generated by detector structures 125 having relatively short source-to-detectors distances (e.g., source-to-detector distances less than or equal to the average distance between the source structures and the detector structures) more tightly than reflectance data that is generated by detector structures having relatively long source-to-detector distances (e.g., source-to-detector distances greater than the average distance). For relatively accurate determination of the optical properties from the reflectance data, this distance-proportional skew may be undesirable and may be corrected by weighting the reflectance data as described immediately below.

Figure 14:
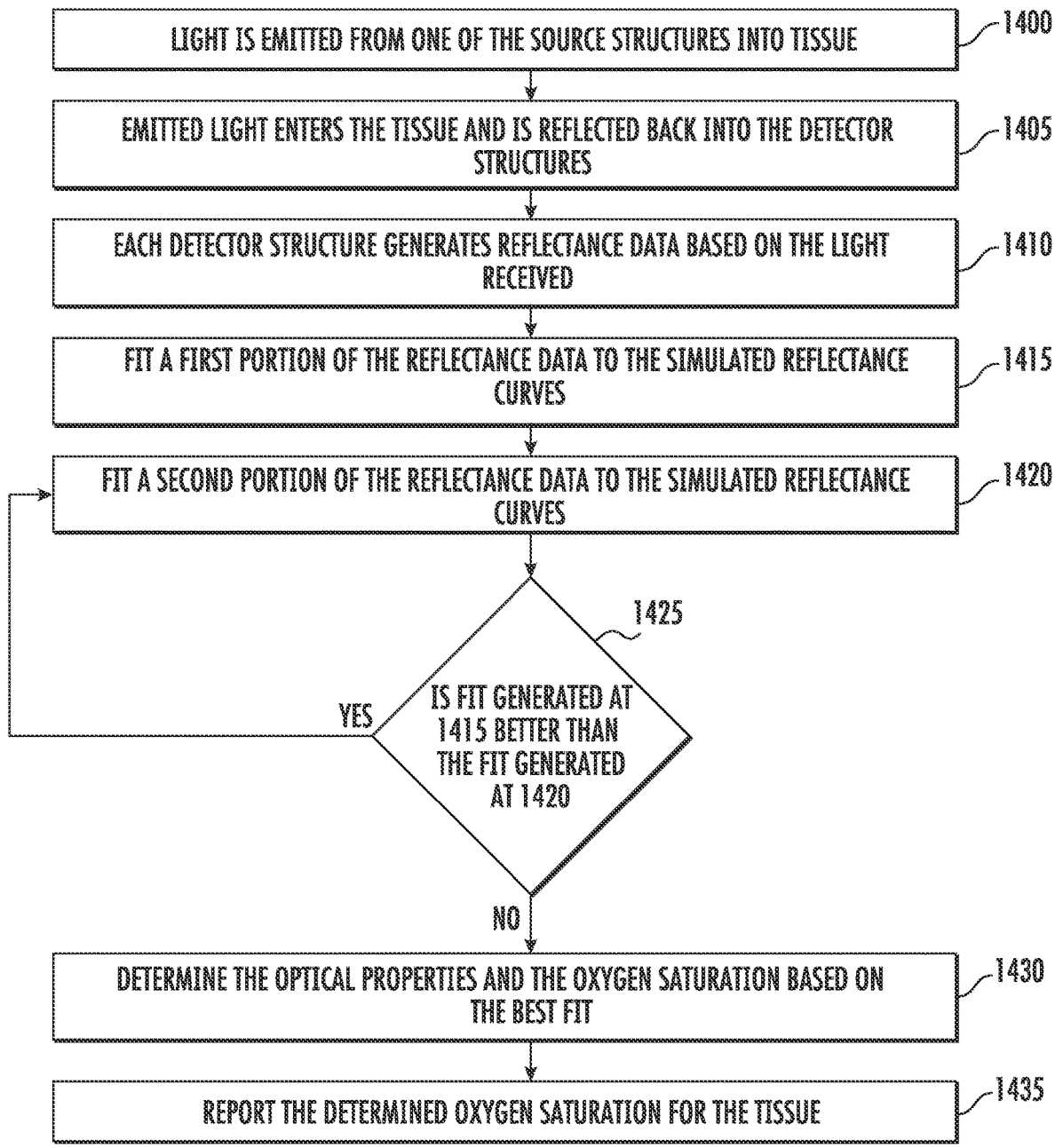
FIG. 14 shows a flow diagram of a method for weighting reflectance data generated by select detector structures.

FIG. 14 shows a flow diagram of a method for weighting reflectance data generated by select detector structures 125. The flow diagram represents one example implementation. Steps may be added to, removed from, or combined in the flow diagram without deviating from the scope of the implementation.

At 1400, oximeter probe 101 emits light from one of the source structures, such as source structure 120*a* into tissue. After the emitted light reflects from the tissue, detector structures 125 detect the light, step 1405, and generate reflectance data for the tissue, step 1410. Steps 1400, 1405, and 1410 may be repeated for multiple wavelengths of light and for one or more other source structures, such as source structure 120*b*. At 1415, oximeter probe 101 fits a first portion of the reflectance data to the simulated reflectance curves 315. The database stored in the memory and fit to the reflectance data can be database 900, database 1000, or database 1100. The first portion of the reflectance data is generated by a first portion of detector structures that are less than a threshold distance from the source structure. The threshold distance may be the average distances (e.g., approximate midrange distance) between the source structures and the detector structures. At 1420, reflectance data for a second portion of the reflectance data is fitted to the simulated reflectance curves. The second portion of reflectance data is generated by the first portion of the detector structures and another detector structure that is at the next largest source-to-detector distance from the source compared to the threshold distance. For example, if the first portion of detector structures includes detector structures 125*c*, 125*d*, 125*e*, and 125*f*, then the detector structure that is at the next largest source-to-detector distance is detector structure 125*g* (see Table 1).

At 1425, the fit generated at step 1415 is compared to the fit generated at step 1420 to determine whether the fit generated at step 1420 is better than the fit generated at 1415. As will be understood by those of skill in the art, a "closeness" of a fit of data to a curve is quantifiable based on a variety of parameters, and the closeness of fits are directly comparable to determine the data having a closer fit (closer fit) to a curve. As will be further understood, a closer fit is sometimes also referred to as a better fit or a tighter fit. If the fit generated at step 1420 is better than the fit generated at step 1415, then steps 1420 and 1425 are repeated with reflectance data that is generated by detector structures that include an additional detector structure (according to the example being considered, detector structure 125*c*) that is positioned at a next increased source-to-detector distance from the source. Alternatively, if the fit generated at step 1420 is not better than the fit generated at step 1415, then the reflectance data for detector structures 125 that are positioned at source-to-detector distances that are greater than the threshold distance are not used in the fit. Thereafter, oximeter probe 101 uses the fit generated at 1415 or step 1420 (if better than the fit determined at step 1415) to determine the optical properties and the oxygen saturation of the tissue, step 1430. Thereafter, oxygen saturation is reported by oximeter probe 101, such as on display 115, step 1435.

According to an alternative implementation, if the fit generated at step 1420 is not better than the fit generated at step 1415, then the reflectance data are weighted by a weighting factor for detector structures that have source-to-detector distances that are greater than the threshold distance so that this weighted reflectance data has a decreased influence on the fit. Reflectance data that is not used in a fit may be considered as having a zero weight and may be associated with reflectance from tissue below the tissue layer of interest. Reflectance from tissue below the tissue layer of interest is said to exhibit a characteristic kink in the reflectance curve that indicates this particular reflectance.

It is noted that curve-fitting algorithms that fit the reflectance data to the simulated reflectance curves may take into account the amount of uncertainty of the reflectance data as well as the absolute location of the reflectance data. Uncertainty in the reflectance data corresponds to the amount of noise from the generation of the reflectance data by one of the detector structures, and the amount of noise can scale as the square root of the magnitude of the reflectance data.

According to a further implementation, oximeter probe 101 iteratively weights the reflectance data based on the amount of noise associated with the measurements of the reflectance data. Specifically, the reflectance data generated by detector structures having relatively large source-to-detector distances generally have lower signal-to-noise ratio compared to the reflectance data generated by detector structure having relatively short source-to-detector distances. Weighting the reflectance data generated by detector structures having relatively large source-to-detector distances allows for this data to contribute to the fit equally or approximately equal to other reflectance data.

Methods described for matching reflectance data to a number of Monte-Carlo-simulated reflectance curves provide for relatively fast and accurate determination of the optical properties of real tissue probed by the oximeter probe. Speed in determining optical properties of tissue is an important consideration in the design of intraoperative probes compared to postoperative probes. Further, the Monte-Carlo methods described allow for robust calibration methods that in-turn allow for the generation of absolute optical properties as compared with relative optical properties. Reporting absolute optical properties, as opposed to relative optical properties, is relatively important for intraoperative oximeter probes as compared with postoperative oximeter probes.

This description of the invention has been presented for the purposes of illustration and description. It is not intended to be exhaustive or to limit the invention to the precise form described, and many modifications and variations are possible in light of the teaching above. The implementations were chosen and described in order to best explain the principles of the invention and its practical applications. This description will enable others skilled in the art to best utilize and practice the invention in various implementations and with various modifications as are suited to a particular use. The scope of the invention is defined by the following claims.

The invention claimed is:

1. A method comprising:
   providing an oximeter device, wherein the oximeter device is wireless;
   providing data points for simulated reflectance curves that are accessible to the oximeter device;
   using the oximeter device, making an oxygen saturation measurement of a tissue comprising emitting light from a source of the oximeter device into the tissue, and receiving light reflected from the tissue at detectors of the oximeter device in response to the emitted light, wherein a plurality of detector responses is obtained for the reflected light;
   fitting the detector responses to the data points for the simulated reflectance curves to determine an absorption coefficient value for the tissue;
   using the absorption coefficient value, determining an oxygen saturation value for the tissue;
   calculating an error value from the fitting of the detector responses to the simulated reflectance curves, and using the error value, determining a quality metric value for the oxygen saturation value; and
   displaying on a screen the oxygen saturation value and the quality metric value.

2. The method of claim 1 comprising when determining the quality metric value, performing a ratiometric calculation.

3. The method of claim 1 wherein calculating the error value comprises using a Tiknonov regularization calculation.

4. The method of claim 1 wherein the quality metric value is displayed on the screen as a moving average value of quality metric values.

5. The method of claim 1 wherein the quality metric value is displayed as a percentage value via a bar graph.

6. A method comprising:
   providing an oximeter device, wherein the oximeter device is wireless;
   providing data points for simulated reflectance curves that are accessible to the oximeter;
   using the oximeter device, making an oximeter measurement of a tissue comprising emitting light from a source of the oximeter device into the tissue, and receiving light reflected from the tissue at detectors of the oximeter device in response to the emitted light, wherein a plurality of detector responses is obtained for the reflected light;
   fitting the detector responses to the data points for the simulated reflectance curves to determine a plurality of absorption coefficient values for the tissue for a plurality of oximeter measurements;
   calculating an oximetry value for the tissue from a first absorption coefficient value of the plurality of absorption coefficient values for a first oximeter measurement of the plurality of oximeter measurements;
   based on the first absorption coefficient value of the plurality of absorption coefficient values, calculating a first quality metric value for the oximetry value for the first oximeter measurement;
   calculating a second quality metric value based on the first quality metric value and at least a second absorption coefficient value of the plurality of absorption coefficient values for at least a second oximeter measurement; and
   displaying on a screen the oximetry value and the second quality metric value.

7. The method of claim 6 wherein the second oximeter measurement is made before the first oximeter measurement.

8. The method of claim 6 wherein calculating the second quality metric value is based on the first quality metric value, the second absorption coefficient value of the plurality of absorption coefficient values for the second oximeter measurement, and a third absorption coefficient value of the plurality of absorption coefficient values for a third oximeter measurement.

9. The method of claim 8 wherein the second and third oximeter measurements are made before the first oximeter measurement.

10. The method of claim 6 comprising calculating an error value from the fit of the detector responses to the simulated reflectance curves, and the error value is used is determining the second quality metric value.

11. The method of claim 6 wherein the second quality metric value is a moving average value of quality metric values.

12. The method of claim 6 wherein the second quality metric value is displayed as a percentage value via a bar graph.

13. The method of claim 8 wherein the second quality metric value is based on a time average of the first, second, and third absorption coefficient values for the first, second, and third oximeter measurements.

14. A method comprising:
   providing an oximeter device, wherein the oximeter device is wireless;
   providing data points for simulated reflectance curves that are accessible to the oximeter device;
   using the oximeter device, making an oximetry measurement of a tissue comprising emitting light from a source of the oximeter device into the tissue, and receiving light reflected from the tissue at detectors of the oximeter device in response to the emitted light, wherein a plurality of detector responses is obtained for the reflected light;

fitting the detector responses to the data points for the simulated reflectance curves to determine an absorption coefficient value for the tissue;

based on the absorption coefficient value, calculating an oximetry value for the tissue;

determining a quality metric value for the oximetry value; and displaying on a screen the oximetry value and the quality metric value.

15. The method of claim 14 comprising:

providing values for a predetermined detector relationship for the detectors and the reflected light;

comparing the detector responses for the detectors with the values for the predetermined detector relationship; and based on the comparison of the detector responses with the values for the predetermined detector relationship, determining the quality metric value.

16. The method of claim 14 wherein the quality metric value is determined by performing a ratiometric calculation.

17. The method of claim 14 wherein the oximetry value is an oxygen saturation value for the tissue.

18. The method of claim 14 comprising calculating an error value from the fit of the detector responses to the simulated reflectance curves, and the error value is used is determining the quality metric value.

19. The method of claim 18 wherein the error value is calculated using a Tiknonov regularization calculation.

20. The method of claim 14 wherein the quality metric value is a moving average value of quality metric values.

21. The method of claim 14 wherein the quality metric value is displayed as a percentage value via a bar graph.

* * * * *